United States Patent
Saini et al.

(10) Patent No.: US 11,359,112 B2
(45) Date of Patent: Jun. 14, 2022

(54) COATINGS WITH TUNABLE AMINE DENSITY

(71) Applicant: Cowper Sciences Inc., Chandler, AZ (US)

(72) Inventors: Gaurav Saini, Chandler, AZ (US); David Smith, Scottsdale, AZ (US); Patrick Walsh, Chandler, AZ (US); Jae H. Park, Gainsville, FL (US)

(73) Assignee: COWPER SCIENCES INC., Chandler, AZ (US)

( * ) Notice: Subject to any disclaimer, the term of this patent is extended or adjusted under 35 U.S.C. 154(b) by 3 days.

(21) Appl. No.: 16/348,485

(22) PCT Filed: Nov. 8, 2017

(86) PCT No.: PCT/US2017/060724
§ 371 (c)(1),
(2) Date: May 8, 2019

(87) PCT Pub. No.: WO2018/089556
PCT Pub. Date: May 17, 2018

(65) Prior Publication Data
US 2019/0359854 A1    Nov. 28, 2019

Related U.S. Application Data

(60) Provisional application No. 62/419,864, filed on Nov. 9, 2016.

(51) Int. Cl.
| | | |
|---|---|---|
| *C09D 183/08* | (2006.01) | |
| *B05D 1/00* | (2006.01) | |
| *C07F 7/08* | (2006.01) | |
| *C08F 30/08* | (2006.01) | |
| *C08G 77/26* | (2006.01) | |
| *C09D 143/04* | (2006.01) | |
| *G01N 33/543* | (2006.01) | |
| *C08G 65/336* | (2006.01) | |
| *C07F 7/18* | (2006.01) | |

(52) U.S. Cl.
CPC ............ *C09D 183/08* (2013.01); *B05D 1/60* (2013.01); *C07F 7/087* (2013.01); *C07F 7/1804* (2013.01); *C08F 30/08* (2013.01); *C08G 65/336* (2013.01); *C08G 77/26* (2013.01); *C09D 143/04* (2013.01); *G01N 33/543* (2013.01); *B01J 2219/00605* (2013.01)

(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,424,186 A | 6/1995 | Fodor et al. |
| 5,571,639 A | 11/1996 | Hubbell et al. |
| 7,270,950 B2 | 9/2007 | Szostak et al. |
| 7,507,480 B2 | 3/2009 | Sugama |
| 7,884,183 B2 | 2/2011 | Von Wronski et al. |
| 7,884,783 B2 | 2/2011 | Choi |
| 7,909,889 B2 | 3/2011 | Charrier et al. |
| 9,482,666 B2 * | 11/2016 | Domenyuk ............ G01N 33/68 |
| 9,970,932 B2 | 5/2018 | Woodbury et al. |
| 2003/0003223 A1 | 1/2003 | Morse et al. |
| 2003/0044833 A1 * | 3/2003 | Benchikh ......... G01N 33/54353 435/6.12 |
| 2003/0219816 A1 | 11/2003 | Solomon et al. |
| 2004/0092396 A1 | 5/2004 | Glazer et al. |
| 2004/0126890 A1 | 7/2004 | Gjerde et al. |
| 2005/0255491 A1 | 11/2005 | Lee et al. |
| 2006/0013971 A1 | 1/2006 | Chen et al. |
| 2006/0074251 A1 | 4/2006 | Jung |
| 2006/0210452 A1 | 9/2006 | Fodor et al. |
| 2007/0248985 A1 * | 10/2007 | Dutta .................... G01N 33/552 435/7.1 |
| 2008/0020507 A1 | 1/2008 | Nomura |
| 2008/0146459 A1 * | 6/2008 | Iwakura ............... B01J 19/0046 506/18 |
| 2008/0207507 A1 | 8/2008 | Lau et al. |
| 2008/0214405 A1 | 9/2008 | Chen et al. |
| 2009/0054251 A1 | 2/2009 | O'Connor et al. |
| 2009/0142792 A1 | 6/2009 | Robinson et al. |

(Continued)

FOREIGN PATENT DOCUMENTS

| | | |
|---|---|---|
| CN | 1282105 A | 1/2001 |
| CN | 102753620 A | 10/2012 |

(Continued)

OTHER PUBLICATIONS

Polymer Chemistry (2011) 2(11) 2574-2580.*
"Epoxide Silylant Agent Ethylenediamine Reaction Product Anchored on Silica Gel-Thermodynamics of Cation-Nitrogen Interaction at Solid/liquid Interfaces" authored by Sales et al. and published in Journal of Non-crystalline Solids (2003) 220, 142-149.*
De Paz, J.L. et la. Exploration of the use of an acylsulfonamide safety-catch linker for the polymer-supported synthesis of hyaluronic acid oligosaccharides. Carbohydr Res. Mar. 30, 2010;345(5):565-71. Epub Jan. 4, 2010.
Mitra et al., Self-assembly of cyclic metal-DNA nanostructures using ruthenium tris(bipyridine)-branchedoligonucleotides. Agnewandte Chemie. 43(43):5804-5808 (2004).
No Author. Pubchem CID 110154. Created: Aug. 8, 2005. Date accessed: Feb. 26, 2018, pp. 1-15.

(Continued)

*Primary Examiner* — Marc S Zimmer
(74) *Attorney, Agent, or Firm* — Wilson Sonsini Goodrich & Rosati

(57) ABSTRACT

Molecules or salts thereof are provided, having the structure in Formula I, wherein $n^2$ and $n^4$ are the same or different and are independently 1, 2, or 3, and $n^3$ is 1 to 20; X is oxygen, nitrogen, or sulfur; wherein $R^1$, $R^2$, $R^3$, $R^4$, $R^5$, $R^6$, and $R^7$ are as described herein. Methods are also provided for the synthesis of and use of the provided molecules in applications for diagnostic testing.

19 Claims, 38 Drawing Sheets

(56) References Cited

U.S. PATENT DOCUMENTS

| | | |
|---|---|---|
| 2009/0176664 A1 | 7/2009 | Chu |
| 2009/0285798 A1 | 11/2009 | Vita et al. |
| 2011/0014222 A1 | 1/2011 | Gonzalez |
| 2011/0319291 A1 | 12/2011 | Vrijbloed et al. |
| 2012/0004130 A1 | 1/2012 | Mattoon et al. |
| 2012/0190574 A1 | 7/2012 | Johnston et al. |
| 2012/0228155 A1 | 9/2012 | Clare et al. |
| 2012/0237555 A1 | 9/2012 | Williams et al. |
| 2012/0238477 A1 | 9/2012 | Albert et al. |
| 2013/0071860 A1 | 3/2013 | Hale et al. |
| 2013/0079250 A1 | 3/2013 | Johnston et al. |
| 2013/0095548 A1 | 4/2013 | Jain et al. |
| 2013/0310265 A1 | 11/2013 | Menegatti et al. |
| 2014/0087963 A1 | 3/2014 | Johnston et al. |
| 2015/0217258 A1 | 8/2015 | Woodbury et al. |
| 2015/0241420 A1 | 8/2015 | Johnston et al. |
| 2016/0041158 A1 | 2/2016 | Woodbury et al. |
| 2016/0052990 A1 | 2/2016 | Ring et al. |
| 2016/0060687 A1 | 3/2016 | Zhu et al. |
| 2016/0067667 A1 | 3/2016 | Rajasekaran et al. |
| 2016/0090592 A1 | 3/2016 | Banyai et al. |
| 2016/0367961 A1 | 12/2016 | Patel et al. |
| 2017/0030906 A1 | 2/2017 | Mesa et al. |
| 2019/0359566 A1 | 11/2019 | Walsh |
| 2020/0116715 A1 | 4/2020 | Gerwien et al. |
| 2020/0407712 A1* | 12/2020 | Boyd ............... G01N 33/6845 |

FOREIGN PATENT DOCUMENTS

| | | |
|---|---|---|
| WO | WO-02081649 A2 | 10/2002 |
| WO | WO-2004053068 A2 | 6/2004 |
| WO | WO-2011041586 A1 | 4/2011 |
| WO | WO-2014006124 A1 | 1/2014 |
| WO | WO-2014039718 A1 | 3/2014 |
| WO | WO-2014062981 A1 | 4/2014 |
| WO | WO-2017173365 A1 | 10/2017 |
| WO | WO-2018089554 A1 | 5/2018 |
| WO | WO-2018089556 A1 | 5/2018 |
| WO | WO-2018236838 A2 | 12/2018 |
| WO | WO-2019157362 A1 | 8/2019 |
| WO | WO-2020102365 A1 | 5/2020 |

OTHER PUBLICATIONS

PCT/US2017/060721 International Search Report and Written Opinion dated Feb. 26, 2018.

PCT/US2017/060724 International Search Report and Written Opinion dated Mar. 13, 2018.

PCT/US2018/038240 International Search Report and Written Opinion dated Dec. 27, 2018.

PCT/US2019/017326 International Search Report and Written Opinion dated Jun. 3, 2019.

PCT/US2019/017326 Invitation to Pay Additional Fees dated Apr. 12, 2019.

Calvo et al. The mitochondrial proteome and human disease. Annu. Rev. Genomics Hum Genet 11:25-44 (2010).

Crooks, et al. WebLogo: a sequence logo generator. Genome Res. Jun. 2004;14(6):1188-90.

England et al., A potent dimeric peptide antagonist of interleukin-5 that binds two interleukin-5 receptor a chains. PNAS 97 (12): 6862-6867 (2000).

Gizdavic-Nikolaidis et al., Spectroscopic characterization of GPTM/DETA and GPTMS/EDA hybrid polymers. Journal of Non-Crystalline Solids 353(16-17): 1598-1605 (2007).

Guillory et al., Glycidyl alkoxysilane 1-8 reactivities towards simple nucleophiles in organic media for improved molecular structure definition in hybrid materials. RSC ADV 6(78): 74087-74099 (2016).

Heidler et al., N-acyl-N-alkyl-sulfonamide anchors derived from Kenner's safety-catch linker: powerful tools in bioorganic and medicinal chemistry. Bioorg Med Chem 13(3):585-99 (2005).

International Application No. PCT/US17/25546 International Search Report and Written Opinion dated Sep. 6, 2017.

Legutki et al., Scalable high-density peptide arrays for comprehensive health monitoring., Nature Communications, Sep. 2014, 5:4785(7 pages).

March et al. Fetal Exposure to Moderate Ethanol Doses: Heightened Operant Responsiveness elicited by Ethanol-Related Reinforcers. Alcohol clin Exp Res 33(11):1981-1993.

Massimo, A. et al. Discovering sequence motifs in quantitative and qualitative peptide data. Technical University of Denmark. PhD Thesis. pp. 1-94 (Sep. 30, 2012).

Mateescu, A. et al. Thin Hydrogel Films for Optical Biosensor Applications, Membranes 2:40-69 (2012).

Naranbhai et al. Ratio of Monocytes to Lymphocytes in Peripheral Blood Identifies Adults at Risk of Incident Tuberculosis Among HIV-Infected Adults Initiating Antiretroviral Therapy. J Infect Dis 209(4):500-509 (2014).

Nieba, L. et al. Competition BIAcore for Measuring True Affinities: Large Differences from Values Determined from Binding Kinetics, Analytical Biochemistry, 234:155-165 (Feb. 15, 1996).

Perosa et al., Generation of biologically active linear and cyclic peptides has revealed a unique fine specificity of rituximab and its possible cross-reactivity with acid sphingomyelinase-like phosphodiesterase 3b precursor. Blood 107(3): 1070-1077 (2006).

Remesic et al., Cyclic Opioid Peptides. Curr Med Chem 23(13):1288-1303 (2016).

Schubert et al. The Mtb proteome library: a resource of assays to quantify the complete proteome of *Mycobacterium tuberculosis*. Cell Host Microbe 13(5):602-12 (2013).

Spengler et al., (Supplemental Materials) The synthesis of an EDTA-like chelating peptidomimetic building block suitable for solid-phase synthesis. Chem Commun 53: 2634-2636 (2017).

Spengler et al., The synthesis of an EDTA-like chelating peptidomimetic building block suitable for solid-phase synthesis. Chem Commun 53: 2634-2636 (2017).

U.S. Appl. No. 16/090,549 Non-Final Office Action dated Dec. 24, 2020.

U.S. Appl. No. 16/968,512 Non-Final Office Action dated Jun. 14, 2021.

Wang et al., Optimization of RGD-Containing Cyclic Peptides against avβ3 Integrin. Mol Cancer Ther. 15(2): 232-240 (2016).

Wrighton et al., Small Peptides as Potent Mimetics of the Protein Hormone Erythropoietin. Science, 273 (1996): 458-450.

Ingenito et al.: Efficient loading of sulfonamide safety-catch linkers by Fmoc amino acid fluorides. Org Lett. 4(7):1187-1188 (2002).

Yin at al: Acylsulfonamide safety-catch linker: promise and limitations for solid-phase oligosaccharide synthesis. Beilstein J Org Chem. 8:2067-2071 (2012).

Harris et al.: Synthesis of a C-Terminal Thioester Derivative of the Lipopeptide Pam2CSKKKKG Using Fmoc SPPS. Synlett 2007(5):0713-0716 DOI:10.1055/s-2007-970759 (2007).

Mohorcic et al.: Surface with antimicrobial activity obtained through silane coating with covalently bound polymyxin B. J Mater Sci Mater Med. 21(10):2775-2782 doi:10.1007/s10856-010-4136-z (2010).

Triola et al.: Solid-phase synthesis of lipidated Ras peptides employing the Ellman sulfonamide linker. Chemistry 16(31):9585-9591 (2010).

Gandhiraman et al.: PECVD coatings for functionalization of point-of-care biosensor surfaces. Vacuum 86(5):547-555 (2012).

Gardner et al.: Functional screening for anti-CMV biologies identifies a broadly neutralizing epitope of an essential envelope protein. Nat Commun. 7:13627 doi:10.1038/ncomms13627 [1-15](2016).

Huang et al., Hydrogen/Deuterium Exchange Mass Spectrometry and Computational Modeling Reveal a Discontinuous Epitope of an Antibofy/TL1A Interaction MABS 101(1): 95-103 (2017).

Hundsberger et al.: Assembly and use of high-density recombinant peptide chips for large-scale ligand screening is a practical alternative to synthetic peptide libraries. BMC Genomics 18(1):450 doi: 10.1186/s12864-017-3814-3 [1-10](2017).

Marthandan et al.: Construction and evaluation of an automated light directed protein-detecting microarray synthesizer. IEEE Trans Nanobioscience 7(1):20-27 doi:10.1109/TNB.2008.2000146 (2008).

(56) References Cited

OTHER PUBLICATIONS

PCT/US19/61196 International Search Report and Written Opinion dated Feb. 27, 2020.
Timmerman et al.: A combinatorial approach for the design of complementarity-determining region-derived peptidomimetics with in vitro anti-tumoral activity. J Biol Chem. 284(49):34126-34134 doi:10.1074/jbc.M109.041459 (2009).

* cited by examiner

| Process condition # | EDA | | Boc-Gly | |
|---|---|---|---|---|
| | Thickness, Å | WCA | Thickness, Å | WCA |
| 1. Injection vol.: 2 ml, Chamber temp.: 100°C | 1.3 | 48 | 2.3 | 61 |
| 2. Injection vol.: 4 ml, Chamber temp.: 100°C | 1.4 | 49 | 2.5 | 60 |
| 3. Injection vol.: 3 ml, Chamber temp.: 100°C, condensation | 5.3 | 49 | 4.3 | 65 |
| 4. Injection vol.: 4 ml, Chamber temp.: 125°C, | 1.3 | 47 | 2.3 | 58 |
| 5. Injection vol.: 3 ml, Chamber temp.: 125°C, condensation | 4.3 | 50 | 4.1 | 65 |
| 6. Injection vol.: 4 ml, Chamber temp.: 150°C, | 0.9 | 48 | NA | NA |

- Use Isopropyl alcohol (IPA) as a diluent for EDBA to vary concentration of EDBA vapors in the CVD chamber, and thus tune reaction of epoxide groups of GPTMS coating.
- Perform CVD of different composition solutions of IPA+EDBA.

FIG. 12

- Substrate – Solution GPTMS functionalized 3" Thermal Oxide Wafers
- IPA:EDBA compositions studied
  - 50:50, 20:80, and 5:95 (EDBA:IPA) v/v
- Injection volume: 1 ml
- Colorimetric Density Assay

FIG. 17

Experimental

- Substrate: Si (<100> orientation) substrate containing ~250 nm thick thermal $SiO_2$
- Aminosilane coatings studied:
  - 3-aminopropyltriethoxysilane (APTES)
  - 3-aminopropylmethyldiethoxysilane (APDEMS)
  - 3-aminopropyldiisopropylethoxysilane (APDIPES)
- Deposition method: Chemical vapor deposition using commercial CVD system
- Analytical characterization: Ellipsometry, WCA, XPS, AFM, Colorimetry, and MADLI-MS

FIG. 21

Why is Surface Properties Control Important?

- Surface properties impact
- Purity and number density of probes
- Non-specific interaction of biological molecules with the substrate
- Presentation of immobilized probes to biological molecules

FIG. 26

Side Chain Deprotection (SCD) Process

- 1st treatment
  - TFA : DMS : m-cresol : DODT : TfOH (0.49 : 0.29 : 0.10 : 0.02 : 0.10) at 0°C for 3 hrs.
- 2nd treatment
  - TFA : thioanisole : DODT : TfOH (0.83 : 0.04 : 0.03 : 0.10) at RT for 1.5 hrs.

TFA: Trifluoroacetic acid
DMS: Dimethyl sulfide
TfOH: Trifluoromethanesulfonic acid
DODT: 2,2'-(Ethylenedioxy)diethanethiol

FIG. 27

Peptide Synthesis for Chemical Stability Study

- Preparatory synthesis
  - Aminosilane-coated surface was functionalized with tetramer peptide linker (GSGS).

- Main synthesis
  - A mixture of 9 amino acids (A, F, G, L, I, N, P, Q, and V) with no side chain protecting groups was coupled 12 times to create a diverse library of peptides.

- Synthesis was done on 8" oxide wafer (full field exposure). Small coupons were diced out of 8" wafer for analytical characterization.

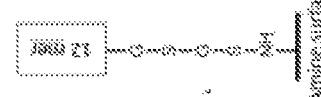
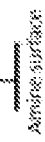

SLG Synthesis – Capping Improves Probe Purity; Capped APDEMS Surface Produces Highest Percentage of Pure Probes

FIG. 43

Summary

- Three aminosilanes yield coatings with comparable thickness but different hydrophilicity.
  - Hydrophilicity of the surface: APTES > APDEMS > APDIPES
- Nitrogen content of the coating is a function of number of ethoxy groups in aminosilane.
  - N content of aminosilane coating: APTES > APDEMS > APDIPES
- All aminosilanes generate smooth coatings.
- Chemical stability of peptide-functionalized aminosilane surface to SCD: APTES > APDEMS > APDIPES
- Acetic anhydride capping helps improve probe purity.
- APTES produces lowest percentage of pure probes. In general, APDIPES surface produces highest percentage of pure probes.

COATINGS WITH TUNABLE AMINE DENSITY

CROSS-REFERENCE

This application is a U.S. National Phase of International Application No. PCT/US17/60724, filed on Nov. 8, 2017, which claims the benefit of U.S. Provisional Application No. 62/419,864, filed Nov. 9, 2016, both of which are incorporated herein by reference in their entireties.

SUMMARY OF THE INVENTION

Disclosed herein are molecules or salts thereof, having the structure:

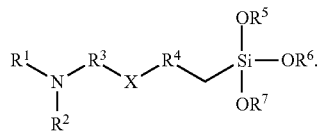

I wherein $R^1$ and $R^2$ can be the same or different and can be independently hydrogen, alkyl, alkenyl, aryl, heteroaryl, alkynyl, arylalkyl, arylalkenyl, haloalkyl, cycloalkyl, sulfonamidyl, acyl, or —$CO_2R^8$, wherein $R^8$ is alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they are bound can form a ring; or wherein at least one of $R^1$ or $R^2$ can comprise a nucleoside, nucleotide, polynucleotide, peptide, peptoid, saccharide, polysaccharide, aptamer, or antibody or fragment thereof;

$R^3$, oriented from N to X, can be alkyl, heteroalkyl, amino-substituted alkyl, amino-substituted heteroalkyl, amidoalkyl, amidoheteroalkyl, amino-substituted amidoheteroalkyl, each optionally substituted with an alkyl, heteroalkyl, amino-substituted alkyl, amino-substituted heteroalkyl, amidoalkyl, amidoheteroalkyl, or amino-substituted amidoheteroalkyl; or wherein $R^3$ can be —$(CR^9R^{10}CR^{11}R^{12})_n$—, wherein n can be 1 to 100, and $R^9$, $R^{10}$, $R^{11}$, and $R^{12}$ can be the same or different and can be independently hydrogen, halo, alkyl, heteroalkyl, amino-substituted alkyl, amino-substituted heteroalkyl, amidoalkyl, amidoheteroalkyl, amino-substituted amidoheteroalkyl; or wherein $R^3$ can be

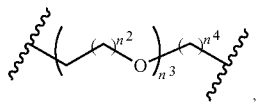

wherein $n^2$ and $n^4$ can be the same or different and can be independently 1, 2, or 3, and $n^3$ can be 1 to 20; or wherein $R^3$ can be a polymer comprising alkyl, heteroalkyl, amino-substituted alkyl, aminoheteroalkyl, and amidoalkyl;

X can be O, $NR^{13}$, or S, wherein $R^{13}$ is hydrogen or alkyl;

$R^4$, oriented from X to C, can be alkyl, alkylether, and alkylthioether, wherein each of alkyl, alkylether, and alkylthioether can be optionally substituted with hydroxyl, thiol, amino, or halo;

$R^5$, $R^6$, and $R^7$ can be the same or different and can be independently hydrogen, alkyl, silyl, or siloxy; and wherein at least one of $R^5$, $R^6$, or $R^7$ optionally further comprises a solid phase.

In some aspects the molecules or salts of structure I can comprise a solid phase. In some aspects, the solid phase can comprise a silicon atom.

Also disclosed herein are molecules or salts thereof, having the structure:

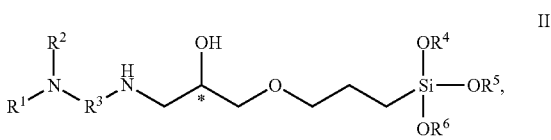

II wherein $R^1$ and $R^2$ can be the same or different and can be independently hydrogen, alkyl, alkenyl, aryl, heteroaryl, alkynyl, arylalkyl, arylalkenyl, haloalkyl, cycloalkyl, sulfonamidyl, acyl, or —$CO_2R^8$, wherein $R^8$ can be alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they are bound can form a ring; or wherein at least one of $R^1$ or $R^2$ can comprise a nucleoside, nucleotide, polynucleotide, peptide, peptoid, saccharide, polysaccharide, aptamer, or antibody or fragment thereof, $R^3$, oriented from $NR^1R^2$ to NH can be alkyl, heteroalkyl, amino-substituted alkyl, amino-substituted heteroalkyl, amidoalkyl, amidoheteroalkyl, amino-substituted amidoheteroalkyl, each optionally substituted with an alkyl, heteroalkyl, amino-substituted alkyl, amino-substituted heteroalkyl, amidoalkyl, amidoheteroalkyl or amino-substituted amidoheteroalkyl; or wherein $R^3$ can be —$(CR^7R^8CR^9R^{10})_n$— wherein n can be 1 to 100, and $R^7$, $R^8$, $R^9$, and $R^{10}$ can be the same or different and can be hydrogen, halo, alkyl, heteroalkyl, amino-substituted alkyl, amino-substituted heteroalkyl, amidoalkyl, amidoheteroalkyl, amino-substituted amidoheteroalkyl; or wherein $R^3$ can be

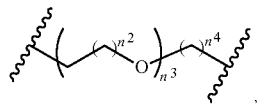

wherein $n^2$ and $n^4$ can be the same or different and can be independently 1, 2, or 3, and $n^3$ can be 1 to 20; or wherein $R^3$ can be a polymer or dendrimer comprising alkyl, heteroalkyl, amino-substituted alkyl, amino-substituted heteroalkyl, amidoalkyl, and amino-substituted amidoalkyl, amidoheteroalkyl, or amino-substituted amidoheteroalkyl;

$R^4$, $R^5$, and $R^6$ can be the same or different and can be independently hydrogen, alkyl, silyl, or siloxy;

(*) is a carbon center, wherein said carbon center can be in an R-configuration or S-configuration; and wherein at least one of $R^4$, $R^5$, or $R^6$ optionally further comprises a solid phase.

In some aspects, the carbon center can be in an R-configuration. In some aspects, the carbon center can be in an S-configuration. In some aspects are molecules or salts comprising a solid phase. In some aspects the solid phase can comprise a silicon atom. In some aspects are molecules of structure II, wherein $R^3$ can comprise alkyl, aminoheteroalkyl, polyamidoaminoalkyl, or polyaminoalkyl.

Also disclosed herein are molecules or salts thereof, having the structure:

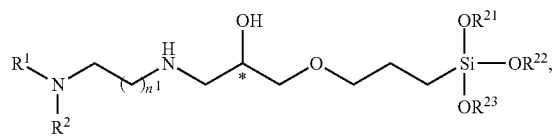

III

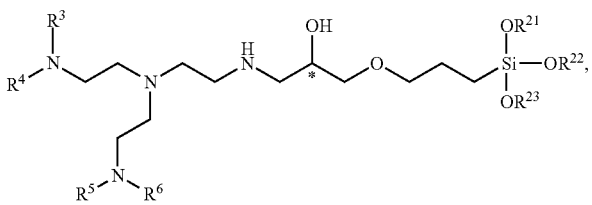

IV

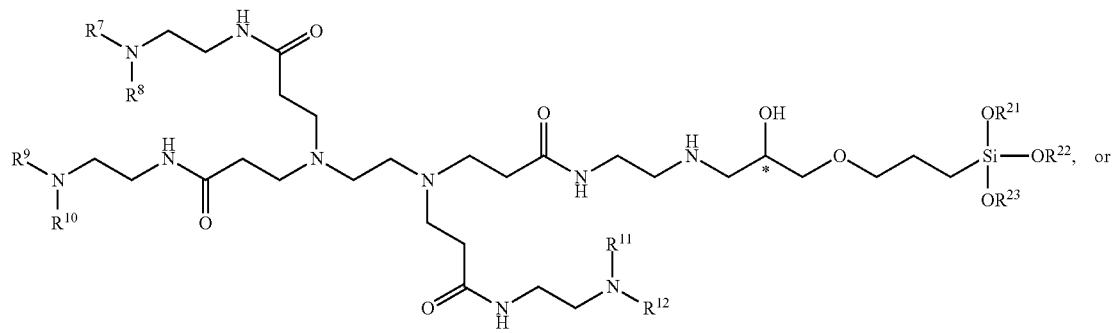

V

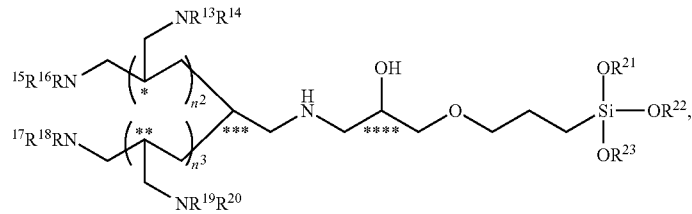

VI wherein:

$n^1$ can be 1, 2, 3, 4, 5, 6, or 7;

$n^2$ and $n^3$ can be the same or different and can be independently about 1 to about 1000;

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ can be the same or different and can be hydrogen, alkyl, alkenyl, aryl, heteroaryl, alkynyl, arylalkyl, arylalkenyl, haloalkyl, cycloalkyl, sulfonamidyl, acyl, or —$CO_2R^{24}$, wherein $R^{24}$ is alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they are bound, $R^3$ and $R^4$ and the N to which they are bound, $R^5$ and $R^6$ and the N to which they are bound, $R^7$ and $R^8$ and the N to which they are bound, $R^9$ and $R^{10}$ and the N to which they are bound, $R^{11}$ and $R^{12}$ and the N to which they are bound, $R^{13}$ and $R^{14}$ and the N to which they are bound, $R^{15}$ and $R^{16}$ and the N to which they are bound, $R^{17}$ and $R^{18}$ and the N to which they are bound, and $R^{19}$ and $R^{20}$ and the N to which they are bound independently optionally form a ring;

$R^3$, $R^4$, and $R^5$ can be the same or different and are independently hydrogen, alkyl, silyl, or siloxy;

(*), (), and (*) are carbon centers, wherein said carbon centers can be independently in an R-configuration or S-configuration, or can be achiral centers;

(****) is a second carbon center, wherein said second carbon center can be in an R-configuration or an S-configuration; and wherein at least one of $R^{21}$, $R^{22}$, or $R^{23}$ optionally further comprises a solid phase.

In some aspects, a carbon center can be in an R-configuration. In some aspects, the carbon center can be in an S-configuration. In some aspects the molecules or salts of structures III, IV, V, or VI can comprise a solid phase. In some aspects, the solid phase can comprise a silicon atom.

In some aspects are methods of synthesizing molecules or salts of structure I, II, III, IV, V, or VI. In some aspects, the method can comprise forming an oxygen-silicon covalent bond between a solid substrate and a first molecule. In some aspects, the first molecule can comprise a silicon at a first end and an epoxide, isocyanate, or thioisocyanate at a second end. In some aspects, the method can further comprise forming a Y-carbon covalent bond between a carbon atom of an epoxide, isocyanate, or thioisocyanate and a second molecule comprising an amino group. In some aspects, Y can be nitrogen, oxygen, sulfur, or selenium. In some aspects, the epoxide, isocyanate, or isothiocyanate and silicon can be linked by a group comprising an alkyl, alkylether, or alkylthioether, wherein each of alkyl, alkylether, or alkylthioether is optionally substituted with hydroxyl, thiol, amino, or halo. In some aspects, the second molecule can be an alkylamine, heteroalkylamine, amino-substituted alkylamine, amino-substituted heteroalkylamine, amidoalkylamine, amidoheteroalkylamine, or amino-substituted amidoheteroalkylamine, each optionally substituted with an alkyl, heteroalkyl, amino-substituted alkyl, amino-substituted heteroalkyl, amidoalkyl, amidoheteroalkyl, or amino-substituted amidoheteroalkyl. In some aspects, forming an oxygen-silicon bond can comprise a deposition reaction. In some aspects, a deposition reaction can be performed in the gas phase. In some aspects, the deposition reaction can comprise a chemical vapor deposition reaction. In some aspects, the chemical vapor deposition reaction can occur at an elevated temperature. In some aspects, the elevated temperature can be at least about 100° C., 110° C., 120° C., 130° C., 140° C., or 150° C. In some aspects, the first molecule can be 3-glycidoxypropyltrimethoxysilane (GPTMS) or any reactive aminosilane. In some aspects, the second molecule can be ethylenediamine (EDA), (ethylenedioxy)bis(ethylamine) (EDBA), tris (2-aminoethyl)amine (TAEA), polyamidoamine (PAMAM), or polyallylamine (PAAm). In some aspects, PAAm can have an average molecular weight of from about 1 KDa to about 100 KDa. In some aspects, the second molecule can have a boiling point of from about 100° C. to 300° C. In some aspects, the method can further comprise coupling the amino group to a protected amino acid or salt thereof. In some aspects, the protected amino acid salt can be a tert-butyl carbamate (Boc)- or 9-fluorenylmethyl carbamate (Fmoc)-protected amino acid. In some aspects, the amino acid can be glycine.

In some aspects are amino coatings comprising two or more of any one of the molecules or salts of structures I, II, III, IV, V, or VI. In some aspects are methods of tuning the amino group density of the amino coating. In some aspects are arrays comprising two or more of any one of the molecules or salts of structures I, II, III, IV, V, or VI. In some aspects, the array can comprise at least 2 of any one of the molecules or salts of structures I, II, III, IV, V, or VI. In some aspects, the array can comprise a density of said amino groups from about $1\times10^{10}$ groups per cm$^2$ to about $1\times10^{14}$ groups per cm$^2$. In some aspects, molecules can be stereoenriched or racemates. In some aspects, molecules or salts can have an enantiomeric excess of at least about 10%, 20%, 30%, 40%, 50%, 60%, 70%, 80%, 85%, 90%, 95%, 96%, 97%, 98%, 99%, or 100%. In some aspects, at least one of the molecules or salts can form a coating. In some aspects, the coating has a thickness of from about 1 angstrom to about 25 angstroms. In some aspects, molecules or their salts are cross-linked. In some aspects, arrays can further comprise instructions for their use.

In some aspects are methods for making an array. In some aspects, making an array can comprise associating the molecule or salt of structure I, II, III, IV, V, or VI with a substrate. In some aspects, making an array can comprise any of the methods disclosed herein for making molecules or salts of structures I, II, III, IV, V, or VI. In some aspects, the array comprises a density of amino group about $1\times10^{10}$ groups per cm2 to about $1\times10^{14}$ groups per cm2. In some aspects are methods comprising tuning the density of said amino groups on said array. In some aspects are kits. In some aspects, kits comprise the molecules of structures I, II, III, IV, V, or VI. In some aspects, kits comprise a binding moiety. In some aspects, a binding moiety can be an antibody. In some aspects, a binding moiety can emit a signal.

In some aspects are methods of making kits. In some aspects, methods of making kits can comprise forming a kit with the molecules or salts of structures I, II, III, IV, V, VI. In some aspects are molecules or salts made by the process of the methods disclosed herein. In some aspects are arrays made by the process of the methods disclosed herein.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 12 depicts the experimental conditions for use of a diluent to tune the reaction of forming a second coating layer.

FIG. 17 depicts substrate characteristics, coating compositions, deposition methods, and analytical characterization methods.

FIG. 21 depicts why surface properties control important.

FIG. 26 depicts an experimental process for side chain deprotection.

FIG. 27 depicts an outline of a peptide synthesis process.

FIG. 43 depicts a summary of amino coating properties.

DETAILED DESCRIPTION

Figure 1:
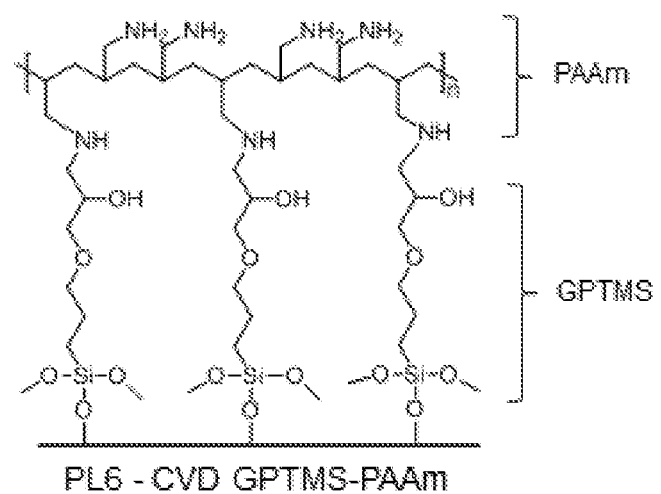
FIG. 1. depicts a GPTMS-PAAm surface coating, prepared by chemical vapor deposition. GPTMS is 3-glycidoxypropyltrimethoxysilane.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

Overview

Detecting and diagnosing immune-mediated disorders, including autoimmune disorders, infections, and cancer, is challenging, with patients having a difficult time receiving an accurate or correct diagnosis. In many instances, patients are often misdiagnosed with other autoimmune conditions because of the closely related nature of these diseases. The disclosure, in one aspect, relates to compounds, methods, and devices that identify differential patterns of peripheral-blood antibody binding to a array-bound molecular library. Differential binding of patient samples to the array results in specific binding patterns or signatures indicative of the disease state of the patient. These binding signatures can accurately determine or diagnose a disease activity, including but not limited to autoimmune disease activity, infectious disease activity, cancer activity, and diabetes disease activity. The identification of such differential binding activity, or signature, is referred to as "immunosignaturing." Synthesized peptide libraries have been commonly used for antibody binding characterization. However, protein and robotically printed peptide arrays have been cost-prohibitive and in situ synthesized peptide arrays have suffered from lack of scalability, poor reproducibility and low production quality. The technologies herein, in one aspect, will enable reliable, low cost, and scaleable methods for construction and use of arrays for immunosignaturing assays.

In some embodiments, arrays with chemical libraries produced by the technologies disclosed herein are used for immune-based diagnostic assays, for example, immunosignature assays. In one aspect, using a patient's antibody repertoire from a drop of blood bound to the arrays, a fluorescence binding profile image of the bound array provide sufficient information to identify and classify a disease state. The arrays disclosed herein incorporate analytical measurements capability within each synthesized array using orthogonal analytical methods including ellipsometry, mass spectrometry, and fluorescence. These measurements enable longitudinal qualitative and quantitative assessment of array synthesis performance.

In some embodiments, detection of antibody binding on a peptide array poses some challenges that can be addressed by the technologies disclosed herein. The technologies disclosed herein address two potential shortcomings of using molecular arrays to profile antibody binding. First, non-specific antibody binding on a array is minimized by coating the solid support with a moderately hydrophilic monolayer comprising, in some embodiments, polyethylene glycol. In some embodiments, the hydrophilic monolayer is homogeneous. Second, synthesized library are linked to the surface using a linker that moves the peptide away from the surface of the solid support so that the peptide may be presented to an antibody in an unhindered orientation. The technologies disclosed herein include such linkers, which, in one aspect, connect chemical libraries to solid supports, including, in some aspects, arrays for immunosignaturing.

Molecules or linkers can also be known as coatings when, for example, formed on a solid support. The technologies herein relate to methods for synthesizing amino-containing coatings, which can be further functionalized at the amino group. The technologies herein further relate to methods for tuning the density of amino groups in coatings. Tuning the density of amino groups in coatings has the advantage of providing flexibility for optimizing the binding characteristics of coatings, and functionalized coatings, to binding moieties. Formation of coatings onto a solid phase can be achieved by solution phase or gas phase reactions. Solid phases can comprise native oxide, thermal oxide, or siloxane surfaces. Solid phases can comprise BTMSE.

Further disclosed herein are arrays comprising the molecules disclosed herein. In some aspects, the arrays comprise a nucleoside, nucleotide, polynucleotide, peptide, peptoid, saccharide, aptamer, or antibody or fragment thereof chemically bound to the linker. In one aspect, the nucleoside, nucleotide, polynucleotide, peptide, peptoid, saccharide, aptamer, or antibody or fragment thereof comprise a chemical library. In some embodiments, the array is a peptide array. In some aspects, the peptide array is synthesized in situ.

One of the major deficiencies of in situ synthesized peptide arrays has been the inability to directly measure purity of the synthesized peptide features. In some embodiments, the technologies include qualitative in situ mass spectrometry of synthesized peptides directly from solid support. Mass spectrometry is performed by incorporating a gas-phase cleavable linker between the solid support and the synthesized peptides so that cleavage of the peptide is done without diffusion from the array feature. Following peptide cleavage, Matrix-Assisted Laser Desorption Ionization (MALDI) mass spectrometry is performed directly on the solid support by applying a thin aerosol matrix layer and subsequently focusing the MALDI laser on individual peptide features to acquire a mass spectrum for each synthesized peptide. Qualitative in situ MALDI mass spectrum from a peptide array feature produced using the photolithographic synthesis approach are also included in the methods and devices described herein. Other analyses known to those of skill in the art may also be used to quantify and/or qualify the fidelity of the in situ synthesis process disclosed herein.

Definitions

The terms "attach", "bind", "couple", and "link" are used interchangeably and refer to covalent interactions (e.g., by chemically coupling), or non-covalent interactions (e.g., ionic interactions, hydrophobic interactions, hydrogen bonds, hybridization, etc.). The terms "specific", "specifically", or specificity" refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules). For example, two molecules may be specifically attached, specifically bound, specifically coupled, or specifically linked. Furthermore, "binding" may refer to either a specific interaction, such as the interaction of an antibody with an epitope, or it may refer to a non-specific interaction.

Nomenclature

Unless otherwise indicated, the term "alkyl" as employed herein alone or as part of another group can include both straight and branched chain hydrocarbons, containing, for instance, 1 to 20 carbons, 1 to 10 carbons, or 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxyl, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group can include saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring and which may be fused to 1 or 2 aromatic rings as described for aryl, which includes cyclopropyl, cyclobuyl, cyclopentyl, cyclohexyl, cycloheptyl, cyclooctyl, cyclodecyl and cyclododecyl, cyclohexenyl, adamantyl, and the like, any of which may be optionally substituted with 1 to 4 substituents such as halogen, alkyl, alkoxy, hydroxyl, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

The term "alkanoyl" as used herein alone or as part of another group can refer to alkyl linked to a carbonyl group.

Unless otherwise indicated, the term "alkenyl" as used herein by itself or as part of another group can refer to straight or branched chain radicals of, for instance, 2 to 20 carbons in the normal chain, which include one to six double bonds in the normal chain, such as vinyl, 2-propenyl, 3-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4, 8, 12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxyl, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "alkynyl" as used herein by itself or as part of another group can refer to straight or branched chain radicals of 2 to 20 carbons in the normal chain, which include one triple bond in the normal chain, such as 2-propynyl, 3-butynyl, 2-butynyl, 4-pentynyl, 2-hexynyl, 3-hexynyl, 2-heptynyl, 3-heptynyl, 4-heptynyl, 3-octenyl, 3-nonenyl, 4-decenyl, 3-undecenyl, 4-dodecenyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxyl, alkanoylamino, alkylamido, arylcarbonylamino, nitro, cyano, thiol, and/or any of the alkyl substitutents set out herein.

The term "halogen" or "halo" as used herein alone or as part of another group can refer to chlorine, bromine, fluorine, and iodine.

Unless otherwise indicated, the term "aryl" as employed herein alone or as part of another group can refer to monocyclic and biclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxyl, nitro, cyano, amino, substituted amino wherein the amino can include 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonyloxy, arylcarbonylamino, arylsulfinyl, arylsulfinylalkyl, arylsulfonylamino or arylsulfonaminocarbonyl and/or any of the alkyl substituents set out herein.

Unless otherwise indicated, the term "amino-substituted" as employed herein alone or as part of another group can refer to a chemical group having from 1 to 10 amino groups substituted thereon.

Unless otherwise indicated, the term "alkylthio" (also known as "thioalkyl") or "arylthio" (also known as "thioaryl") as employed herein alone or as part of another group can include any of the above alkyl or aryl groups linked to a sulfur atom.

Unless otherwise indicated, the term "selenoalkyl" as employed herein alone or as part of another group can include any of the above alkyl groups linked to a selenium atom.

Unless otherwise indicated, the term "alkylamino" or "arylamino" as employed herein alone or as part of another group can include any of the above alkyl or aryl groups linked to a nitrogen atom.

Unless otherwise indicated, the term "acyl" as employed herein by itself as part of another group, as defined herein, can refer to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group can refer to a 5-, 6-, or 7-membered saturated or partially unsaturated ring which can include 1 to 2 heteroatoms such as nitrogen, oxygen and/or sulfur, linked through a carbon atom or a heteroatom, where possible, optionally via the linker ($CH_2$), (where r is 1, 2, or 3).

Unless otherwise indicated, the term "heteroaryl" as used herein alone or as part of another group can refer to a 5- or 6-membered aromatic ring which can include 1, 2, 3 or 4 heteroatoms such as nitrogen, oxygen or sulfur, and such rings fused to an aryl, cycloalkyl, heteroaryl or cycloheteroalkyl ring, and includes possible N-oxides. The heteroaryl group may optionally include 1 to 4 substituents such as any of the substituents set out above for alkyl.

Unless otherwise indicated, the term "heteroalkyl" as used herein alone or as part of another group can refer to an alkyl group, as defined herein, which can include 1, 2, 3, or 4 heteroatoms such as nitrogen, oxygen or sulfur. The heteroalkyl group may optionally include 1 to 4 substituents such as any of the substituents set out above for alkyl.

All stereoisomers of compounds are contemplated, either in admixture or in pure or substantially pure form. Compounds can have asymmetric carbon centers at any of the carbon atoms including any one of the R substituents. Compounds can be either optically active or optically inactive. Asymmetric carbon centers can be independently in an R- or S-configuration. As defined herein asymmetric carbons are carbons that are a stereogenic center. Consequently, compounds of structures I, IA, or II can exist in enantiomeric or diastereomeric forms or in mixtures thereof. Enantiomeric mixtures can exist with an enantiomeric excess of 10%, 20%, 30%, 40%, 50%, 60%, 70%, 80%, 85%, 90%, 95%, 96%, 97%, 98%, 99%, 99.5% or 100%. Diastereomeric mixtures can exist with a diastereomeric ratio of 1:1, 2:1, 3:1, 4:1, 5:1, 6:1, 7:1, 8:1, 9:1, 10:1, 20:1, 50:1, 100:1, or 500:1. The processes for preparation of the molecules disclosed herein can utilize racemates, enantiomers or diastereomers as starting materials. When diastereomeric or enantiomeric products are prepared, they can be separated by conventional methods, for example, by chromatographic or fractional crystallization.

A polynucleotide, as used herein, can be any type of nucleic acid molecule, including DNA, RNA, a hybridization thereof, or any combination thereof. For example, a polynucleotide can be cDNA, genomic DNA, mRNA, tRNA, rRNA, or microRNA.

A peptide, polypeptide, or protein can be contemplated to include any fragments thereof, in particular, immunologically detectable fragments. A peptide can be contemplated to include an α-peptide, a β-peptide, or a γ-peptide.

Methods

Methods disclosed herein can include synthesizing coatings on solid supports. Characteristics of coatings prepared by the methods disclosed herein can be analyzed by various methods understood by person of skill in the art. Methods of analysis can include, ellipsometry, water contact angle (WCA), X-ray photoelectron spectroscopy (XPS), atomic force microscopy (AFM), colorimetry, mass-spectrometry, including MALDI-MS, and the like.

In some embodiments, forming coatings can comprise coupling an aminosilane to a substrate. In some embodiments, the aminosilane can comprise 3-aminopropyltriethoxysilane (APTES), 3-aminopropylmethyldiethoxysilane (APDEMS), or 3-aminopropyldiisopropylethoxysilane (APDIPES).

In some embodiments, forming coatings can comprise a first step comprising forming a first coating layer. In some embodiments, the first step can comprise forming an oxygen-silicon bond between a sold substrate and a first molecule. In some embodiments, the first molecule can comprise a silicon at a first end and an epoxide, isocyanate, or thioisocyanate at a second end. In some embodiments, the first step can be performed in solution phase or in gas phase. In some embodiments, forming coatings can further comprise a second step comprising coupling a second molecule to the epoxide, isocyante, or thioisocyanate of the first molecule to form a second coating layer. Coatings, as used herein, can be understood to encompass both single layer coatings and coatings comprising a first layer and a second layer. In some embodiments, the second molecule can have a boiling point of about 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C. In some embodiments, the second step can comprise using a diluent. In some embodiments, a diluent can be an alcohol. In some embodiments, the alcohol can be ethanol, 1-propanol, 2-propanol (also known as isopropanol), 1-butanol, 2-butanol, tert-butanol, 1-pentanol, 2-pentanol, 3-pentanol, 3-methylbutan-1-ol (also known as isoamyl or isopentyl alcohol), 2-methylbutan-1-ol, 2,2-dimethylpropan-1-ol (also known as neopentyl alcohol), 3-methylbutan-2-ol, or 2-methylbutan-2-ol (also known as tert-amyl alcohol).

In some embodiments, formation of a coating can be accomplished by a deposition reaction. In some embodiments, the deposition reaction can be a chemical vapor deposition reaction. In some embodiments, coatings can be characterized by their water contact angle. In some embodiments, coatings can have a water contact angle of about 10°, 20°, 30°, 40°, 50°, 60°, 70°, 80°, 90°, 100°, 110°, 120°, 130°, 140°, 150°, or 160°. In some embodiments, coatings can have a contact angle from about 10° to about 120°. In some embodiments, coatings can have a water contact angle from about 40° to about 90°. In some embodiments, coatings can be characterized by their thickness. In some embodiments, thickness can be measured by ellipsometry. In some embodiments, coatings can have a thickness of about 0.5 angstroms (Å), 0.6 Å, 0.7 Å, 0.8 Å, 0.9 Å, 1 Å, 2 Å, 3 Å, 4 Å, 5 Å, 6 Å, 7 Å, 8 Å, 9 Å, 10 Å, 11 Å, 12 Å, 13 Å, 14 Å, 15 Å, 16 Å, 17 Å, 18 Å, 19 Å, 20 Å, 25 Å, 30 Å, 35 Å, 40 Å, 45 Å, 50 Å, 60 Å, 70 Å, 80 Å, 90 Å, or 100 Å. In some embodiments, coatings can have a thickness of from about 1 Å to about 10 Å. In some embodiments, coatings can have a thickness of from about 5 Å to about 7 Å. In some embodiments, coatings can be characterized by their smoothness. In some embodiments, coating smoothness can be measured by AFM. In some embodiments, coatings can have a smoothness of a root mean square of roughness ($R_q$) of about 0.10 nm, 0.11 nm, 0.12 nm, 0.13 nm, 0.14 nm, 0.15 nm, 0.16 nm, 0.17 nm, 0.18 nm, 0.19 nm, 0.20 nm, 0.21 nm, 0.22 nm, 0.23 nm, 0.24 nm, 0.25 nm, 0.26 nm, 0.27 nm, 0.28 nm, 0.29 nm, or 0.30 nm. In some embodiments, coatings can have an $R_q$ of from about 0.1 nm to about 0.3 nm. In some embodiments, coatings can have an $R_q$ of from about 0.2 to about 0.25 nm. In some embodiments, coatings can have a density of amino groups of about $1 \times 10^9$, $1 \times 10^{10}$, $1 \times 10^{11}$, $1 \times 10^{12}$, $1 \times 10^{13}$, $1 \times 10^{14}$, or $1 \times 10^{15}$ amino groups per square centimeter.

In some embodiments, coatings can be coupled at the amine to a target analyte to form a target analyte-functionalized coating. In some embodiments, a target analyte can be a peptide. A peptide can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. In some embodiments, peptides can comprise a library of peptides. In some embodiments, peptides can have protected side chains. In some embodiments, peptide side chains can be protected as benzyl ethers. In some embodiments, a coating can be coupled to a peptide by stepwise coupling of each of amino acid of the peptide.

Some embodiments comprise functionalizing an amimo coating. Amino coatings can be functionalized by coupling the amino groups of the amino coating to molecules. A molecule can be a building block. In some embodiments, coupling comprises: coupling of an amino group to the carboxylic acid of a first building block. In some embodiments, a building block can comprise a carboxylic acid and a protected amine. In some embodiments, a building block can be an N-protected amino acid. In some embodiments, the protected amino acid can comprise a Boc-protected amine or an Fmoc-protected amine. In some embodiments, coupling can further comprise deprotection of the coupled building block. In some embodiments, coupling can further comprise coupling of the amino group of the deprotected first building block to the carboxylic acid of a second building block. In some embodiments, functionalizing of an amino coating can comprise iterative couplings to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 building blocks. In some embodiments, protected building blocks can be protected amino acids.

In some embodiments, functionalizing an amino coating can further comprise performing a capping step after any one of the described coupling steps. Capping can comprise reacting amino groups with a reagent to form a protected, or capped, amino group. Capping can comprise reacting amino groups that were not consumed in the preceding coupling reaction. Capping reagents can comprise acetic anhydride, acetyl chloride, acetyl fluoride, or an acylglycine. In some aspects, the capping step can form an alkylamine, arylamine, acetamide, carbamate, phthalimide, enamine, sulfonamide, or N-protected amino acid. In some aspects, the N-protected amino acid can be an N-acyl-protected amino acid. In some aspects, the protected amino acid can be acetyl glycine.

In some embodiments, forming coatings can comprise a first step comprising forming a first coating layer. In some embodiments, the first step can comprise forming an oxygen-silicon bond between a sold substrate and a first molecule. In some embodiments, the first molecule can comprise a silicon at a first end and an epoxide, isocyanate, or thioisocyanate at a second end. In some embodiments, the first step can be performed in solution phase or in gas phase. In some embodiments, forming coatings can further comprise a second step comprising forming a second coating layer. In some embodiments, forming said second coating layer can comprise a chemical vapor deposition reaction.

Supports/Substrates/Solid Phases

The present disclosure provides solid supports (also known as solid phases, substrates, or supports). The nature and geometry of a support or substrate can depend upon a variety of factors, including the type of array (e.g., one-dimensional, two-dimensional or three-dimensional). Generally, a substrate can be composed of any material which will permit coupling of a nucleoside, nucleotide, polynucleotide, peptide, peptoid, saccharide, aptamer, or antibody or fragment thereof, which will not melt or degrade under the conditions used to couple said nucleoside, nucleotide, polynucleotide, peptide, peptoid, saccharide, aptamer, or antibody or fragment thereof to said solid support. A solid support can be composed of any material which will permit coupling of a target analyte, and/or other moiety at one or more discrete regions and/or discrete locations within the discrete regions. A solid support can be composed of any material which will permit washing or physical or chemical manipulation without dislodging a target analyte or binding moiety from the solid support.

A substrate may take a variety of configurations ranging from simple to complex, depending on the intended use of the array. Thus, a substrate can have an overall slide or plate configuration, such as a rectangular or disc configuration. A standard microplate configuration can be used. In some embodiments, the surface may be smooth or substantially planar, or have irregularities, such as depressions or elevations. For example, the substrates of the presently disclosed subject matter can include at least one surface on which a pattern of recombinant virion microspots can be coupled or deposited. In some instances, a substrate may have a rectangular cross-sectional shape, having a length of from about 10-200 mm, 40-150 mm, or 75-125 mm; a width of from about 10-200 mm, 20-120 mm, or 25-80 mm, and a thickness of from about 0.01-5.0 mm, 0.1-2 mm, or 0.2 to 1 mm.

A support may be organic or inorganic; may be metal (e.g., copper or silver) or non-metal; may be a polymer or nonpolymer; may be conducting, semiconducting or non-conducting (insulating); may be reflecting or nonreflecting; may be porous or nonporous; etc. A solid support as described above can be formed of any suitable material, including metals, metal oxides, semiconductors, polymers (particularly organic polymers in any suitable form including woven, nonwoven, molded, extruded, cast, etc.), silicon, silicon oxide, and composites thereof.

Suitable materials for use as substrates include, but are not limited to, polycarbonate, gold, silicon, silicon oxide, silicon oxynitride, indium, tantalum oxide, niobium oxide, titanium, titanium oxide, platinum, iridium, indium tin oxide, diamond or diamond-like film, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polyacrylonitrile (PAN), polyacrylate, polycarbonate, polybutylene terephthalate (PBT), poly(ethylene) (PE) (including low density, linear low density, high density, cross-linked and ultra-high molecular weight grades), poly(propylene) (PP), cis and trans isomers of poly(butadiene) (PB), cis and trans isomers of poly(isoprene), polyethylene terephthalate) (PET), polypropylene homopolymer, polypropylene copolymers, polystyrene (PS) (including general purpose and high impact grades), polycarbonate (PC), poly(epsilon-caprolactone) (PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), styrene maleic anhydride (SMA), metal oxides, glass, silicon oxide or other inorganic or semiconductor material (e.g., silicon nitride), compound semiconductors (e.g., gallium arsenide, and indium gallium arsenide), and combinations thereof.

Examples of well-known solid supports include polypropylene, polystyrene, polyethylene, dextran, nylon, amylases, glass, natural and modified celluloses (e.g., nitrocellulose), polyacrylamides, agaroses and magnetite. In some instances, the solid support can be silica or glass because of its great chemical resistance against solvents, its mechanical stability, its low intrinsic fluorescence properties, and its flexibility of being readily functionalized. In one embodiment, the substrate can be glass, particularly glass coated with nitrocellulose, more particularly a nitrocellulose-coated slide (e.g., FAST slides).

In some embodiments, the support can be planar. In some instances, the support can be spherical. In some instances, the support can be a bead. In some instances, a support can be magnetic. In some instances, a magnetic solid support can comprise magnetite, maghemite, FePt, SrFe, iron, cobalt, nickel, chromium dioxide, ferrites, or mixtures thereof. In some instances, a support can be nonmagnetic. In some embodiments, the nonmagnetic solid support can comprise a polymer, metal, glass, alloy, mineral, or mixture thereof. In some instances a nonmagnetic material can be a coating around a magnetic solid support. In some instances, a magnetic material may be distributed in the continuous phase of a magnetic material. In some embodiments, the solid support comprises magnetic and nonmagnetic materials. In some instances, a solid support can comprise a combination of a magnetic material and a nonmagnetic material. In some embodiments, the magnetic material is at least about 5, 10, 20, 30, 40, 50, 60, 70, or about 80% by weight of the total composition of the solid support. In some embodiments, the bead size can be quite large, on the order of 100-900 microns or in some cases even up to a diameter of 3 mm. In other embodiments, the bead size can be on the order of 1-150 microns. The average particle diameters of beads can be in the range of about 2 m to several millimeters, e.g., diameters in ranges having lower limits of 2 µm, 4 µm, 6 µm, 8 µm, 10 µm, 20 µm, 30 µm, 40 µm, 50 µm, 60 µm, 70 µm, 80 µm, 90 µm, 100 µm, 150 µm, 200 µm, 300 µm, or 500 µm, and upper limits of 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

In some embodiments, the support can comprise an array. In some embodiments, the array comprises a target analyte. In some embodiments, the target analyte comprises a nucleoside, a nucleotide, a polynucleotide, a peptide, a peptoid, a saccharide, a polysaccharide, an aptamer, or an antibody or fragment thereof. In some embodiments, the target analyte comprises a library of target analytes.

In some embodiments, an array comprises a library of molecules. In some embodiments, the array can comprise at least about 100, 1000, 10,000, 100,000, $10^6$, $10^7$, $10^8$, $10^9$, $10^{10}$, $10^{11}$, $10^{12}$, $10^{13}$ $10^{14}$, or $10^{15}$ molecules per 1 $cm^2$. In some embodiments, a molecule can comprise a sequence of monomers. In some embodiments, the sequence of monomers can comprise a sequence of amino acids. In some embodiments, a feature can be a region on a substrate from about 0.5 microns to about 200 microns in diameter. In some embodiments, the array can have a plurality of features. In some embodiments, the center-to-center distance between features can be from about 1 micron to about 300 microns. In some embodiments, the array can comprise at least about 1,000, 10,000, 100,000, 200,000, 300,000, 400,000, or 500, 000, 1 million, 2 million, 3 million, 4 million, or 8 million features per 1 $cm^2$. In some embodiments, at least about 40% of the molecules in the library are distinct. In some embodiments, at least about 50% of the molecules in the library are distinct. In some embodiments, at least about 60% of the molecules in the library are distinct. In some embodiments, at least about 70% of the molecules in the library are distinct. In some embodiments, at least about 80% of the molecules in the library are distinct. In some embodiments, at least about 90% of the molecules in the library are distinct. In some embodiments, at least 50% of the molecules in the library are at least 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, at least 50% of the molecules in the library are at most 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, the library comprises a median monomer length of about 3, 4, 5, 6, 7, 8, 9, 10, 11, 12, 13, 14, 15, 16, 17, 18, 19, 20, 30, 40, 50, 60, 70, 80, 90, or 100 monomers. In some embodiments, the array can comprise at least 10,000, 50,000, 100,000, 200,000, 300,000, 400,000, 500,000, 600,000, 700,000, 800,000, 900,000, $10^6$, or $10^7$ sequentially distinct library molecules. In some embodiments, the array substrate can be selected from wafers, slides, and beads. In some embodiments, the library can be an in-situ synthesized chemical library. In some embodiments, the molecules can be polynucleotides, peptides, peptoids, or polysaccharides.

Binding Moiety

An analyte binding moiety, also referred to as a binding moiety (or domain) can be the region, molecule, domain, portion, fragment, or moiety that binds to a target analyte. Thus, a binding moiety confers the ability to bind or specifically bind to given target. A binding moiety can be a nucleic acid molecule or can be proteinaceous. Binding moieties include, but are not limited to, RNAs DNAs, RNA-DNA hybrids, small molecules (e.g., drugs or metabolites), aptamers, polypeptides, proteins, antibodies, viruses, virus particles, cells, fragments thereof, and combinations thereof.

In some embodiments, a binding moiety can be a polypeptide, a protein, or any fragment thereof. In some embodiments, a polypeptide or protein can be an engineered or recombinant polypeptide or protein. In some embodiments, a binding moiety is an antibody or fragment thereof. An antibody can be of any isotype (e.g., IgG, IgE, IgM, IgD, IgA and IgY), class ($IgG_1$, $IgG_2$, $IgG_3$, $IgG_4$, $IgA_1$, $IgA_2$), subclass or modified version thereof. Antibodies may include complete immunoglobulins or fragments thereof. An antibody fragment can refer to one or more fragments of an antibody that retains the ability to specifically bind to a target molecule, such as an antigen.

In some embodiments, a binding moiety can be an aptamer. An aptamer is an isolated nucleic acid molecule that can bind with high specificity and affinity to a target analyte, such as a protein. An aptamer comprises a three dimensional structure held in certain conformation(s) that provide chemical contacts to specifically bind a given target. In some embodiments, a binding moiety is small molecule. For example, a small molecule can be a macrocyclic molecule, an inhibitor, a drug, or chemical compound. In some embodiments, a binding moiety is a cell. For example, a binding moiety can be an inact cell, a cell treated with a compound (e.g. a drug), a fixed cell, a lysed cell, or any combination thereof.

Detection Methods

Detection methods for detecting bound binding moieties can include photometric and non-photometric means. In some embodiments, such methods process includes a method to detect and measure absorbance, fluorescence, refractive index, polarization or light scattering. These include direct and/or indirect means to measure such parameters. Methods involving fluorescence include fluorescent tagging in immunological methods such as ELISA or sandwich assay. Methods involving refractive index include surface Plasmon resonance (SPR), grating coupled methods (e.g., sensors uniform grating couplers, wavelength-interrogated optical sensors (WIOS) and chirped grating couplers), resonant minor and interferometric techniques. Methods involving polarization include ellipsometry. Light scattering methods may also be used. Other means for tagging and/or separating and/or detecting can also include magnetic means. Magnetic resonance imaging (MRI), or gas phase ion spectrometry may all be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Binding assays can also be useful, e.g., for identifying disease related antibodies (binding moieties) that interact with the target analytes described herein. For example, antibodies or other molecules that bind target analytes can be identified in binding assays. Binding assays can involve, but are not limited to, use of isolated polypeptides, crude extracts, or cell-based assays. In some embodiments the assays described herein can be used to a) identify subjects whose have a first disease or a second disease; (b) assess the impact of an disease therapy; and (c) monitor disease progression.

Binding assays can involve contacting a target analyte with a sample comprising a binding moiety (antibody) and allowing sufficient time for the molecule and test agents to form a binding complex. Any binding complexes formed can be detected using any of a number of established analytical techniques. Binding assays include, but are not limited to, methods that measure co-precipitation or co-migration on non-denaturing SDS-polyacrylamide gels, co-migration on Western blots, enzyme linked immunosorbent assay (ELISA), radioimmunoassay (RIA), immunoradiometric assay, fluoroimmunoassay, chemiluminescent assay, bioluminescent assay, fluorescence activated cells sorting (FACS), or fluorescence resonance energy transfer (FRET).

Diagnostics

The methods and apparatus disclosed herein can be used to screen for various diseases or conditions, including an alteration in the state of the body or of some of the organs, interrupting or disturbing the performance of the functions and/or causing symptoms such as discomfort, dysfunction, distress, or even death to the person afflicted or those in contact with the person. A disease or condition can also include a distemper, ailing, ailment, amalady, disorder, sickness, illness, complain, interdisposition and/or affectation.

For example, samples containing binding moieties from a diseased animal can be simultaneously screened for the binding moieties' ability to interact with an array. These interactions can be compared to those of samples from individuals that are not in a disease state, not presenting symptoms of persons in the disease state, or presenting symptoms of the disease state. For example, the levels of binding moieties in samples from a diseased animal can be simultaneously determined. These levels can be compared to those of samples from individuals that are not in a disease state, not presenting symptoms of persons in the disease state, or presenting symptoms of the disease state.

The methods, kits, and compositions described herein can be used in medical diagnostics, drug discovery, molecular biology, immunology and toxicology. Arrays can be used for large scale binding assays in numerous diagnostic and screening applications. The multiplexed measurement of quantitative variation in levels of large numbers of target analytes (e.g., proteins) allows the recognition of patterns defined by several to many different target analytes. The multiplexed identification of large numbers of interactions between target analytes and binding moieties allows for the recognition of binding and interaction patterns defined by several to many different interactions between target analytes and binding moieties. Many physiological parameters and disease-specific patterns can be simultaneously assessed. One embodiment involves the separation, identification and characterization of proteins present in a biological sample. For example, by comparison of disease and control samples, it is possible to identify disease specific target analytes. These target analytes can be used as targets for drug development or as molecular markers of disease. Substrate-bound molecules of the present invention may also be used as solid phase filtration devices, wherein capture agents are attached to the surface.

In some embodiments, methods can be methods for diagnosing or detecting a disease or condition such as a cancer, inflammatory disease, immune disease, autoimmune disease, cardiovascular disease, neurological disease, infectious disease, metabolic disease, or a perinatal condition. For example, the disease or condition can be a tumor, neoplasm, or cancer. The cancer can be, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, or Burkitt's lymphoma. The disease or condition can also be a premalignant condition, such as Barrett's Esophagus. The disease or condition can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The disease or condition can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event. The disease or condition can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neuropsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g., stroke), brain trauma, microbial infection, or chronic fatigue syndrome. The condition may also be fibromyalgia, chronic neuropathic pain, or peripheral neuropathic pain. The disease or condition may also be an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. The disease or condition can also be a perinatal or pregnancy related condition (e.g., preeclampsia or preterm birth), zika virus, dengue fevor, flavivirus, or a metabolic disease or condition, such as a metabolic disease or condition associated with iron metabolism.

In some embodiments, methods are methods for diagnosing or detecting an autoimmune disorder. In some embodiments, methods can be methods for determining a disease or condition or the progression of a disease or condition. Non-limiting examples of disorder associated with the immune system can include: autoimmune disorders, inflammatory diseases, HIV, rheumatoid arthritis, diabetes mellitus type 1, systemic lupus erythematosus, scleroderma, multiple sclerosis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis.

Kits

Also provided are kits that find use in practicing the subject methods, as mentioned above. A kit can include one or more of the compositions described herein. A kit can include at least one nucleoside, nucleotide, polynucleotide, peptide, peptoid, saccharide, aptamer, or antibody or fragment thereof. A kit can include at least one binding moiety.

A kit can include a solid support. In some embodiments, the solid support is already functionalized with at least one molecule of structure I. In some embodiments, the solid support is already functionalized with at least one nucleoside, nucleotide, polynucleotide, peptide, peptoid, saccharide, aptamer, or antibody or fragment thereof. A kit can include a reagent for coupling at least one nucleoside, nucleotide, polynucleotide, peptide, peptoid, saccharide, aptamer, or antibody or fragment thereof to the solid support.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, such as printed information on a suitable medium or substrate (e.g., a piece or pieces of paper on which the information is printed), in the packaging of the kit, in a package insert, etc. Yet another means would be a computer readable medium (e.g., diskette, CD, etc.), on which the information has been recorded. Yet another means that may be present is a website address which may be used via the internet to access the information at a removed site.

Communicating a Result

Additional embodiments relate to the communication of assay results or diagnoses or both to technicians, physicians or subjects, for example. In certain embodiments, computers will be used to communicate results of the assessing or diagnoses or both to interested parties, e.g., physicians and their subjects. In some embodiments, the assessing can be performed or results analyzed in a country or jurisdiction which differs from the country or jurisdiction to which the results or diagnoses are communicated. In some embodiments, a diagnosis based on the presence or absence in a test subject of a binding moiety or a binding signature, or signal identified may be communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. In certain embodiments, all or some of the method steps, including the assaying of samples, diagnosing of diseases, and communicating of method results or diagnoses, may be carried out in diverse (e.g., foreign) jurisdictions.

OTHER EMBODIMENTS

The section headings used herein are for organizational purposes only and are not to be construed as limiting the subject matter described.

It is to be understood that the methods and compositions described herein are not limited to the particular methodology, protocols, constructs, and reagents described herein and as such may vary. It is also to be understood that the terminology used herein is for the purpose of describing particular embodiments only, and is not intended to limit the scope of the methods and compositions described herein, which will be limited only by the appended claims. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

EXAMPLES

Example 1—GPTMS-PAAm

FIG. 1 illustrates a GPTMS-PAAm molecule.

Example 2—GPTMS-TAEA

Figure 2:
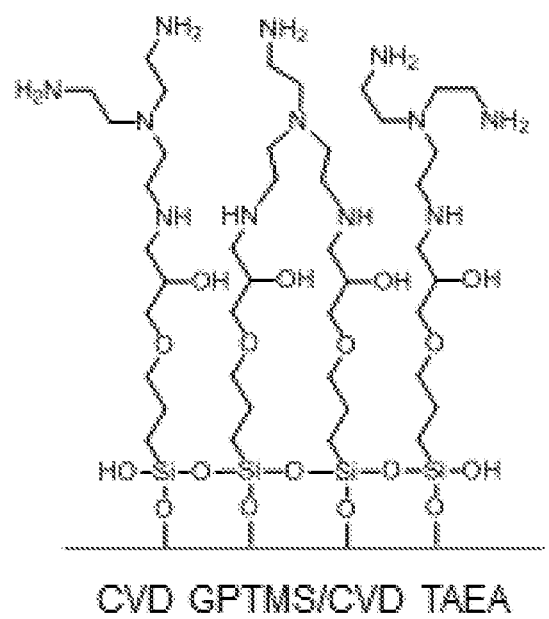
FIG. 2. depicts a GPTMS-TAEA surface coating prepared by chemical vapor deposition.
Figure 3:
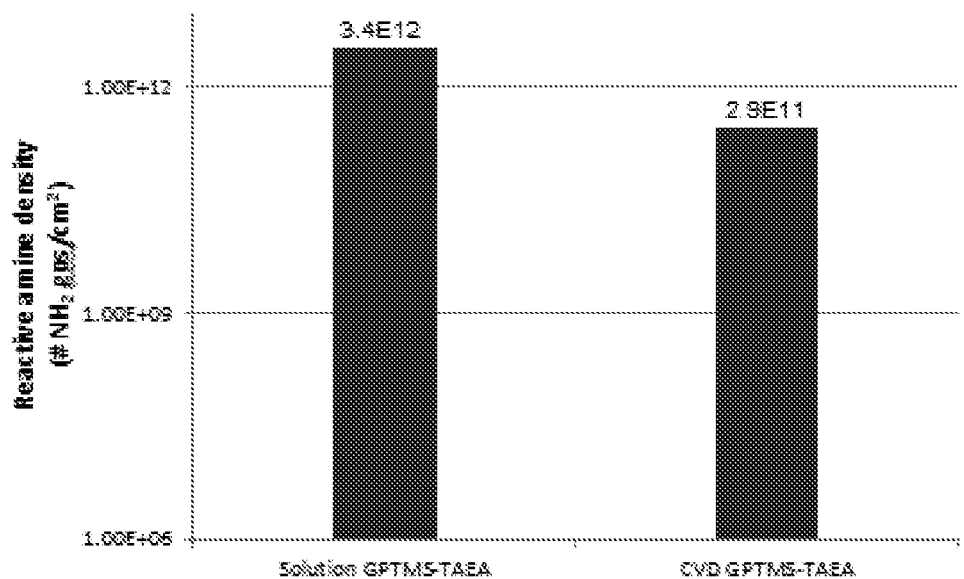
FIG. 3. depicts the reactive amine density of GPTMS-TAEA surface coatings prepared by either solution phase reaction or chemical vapor deposition.
Figure 4:
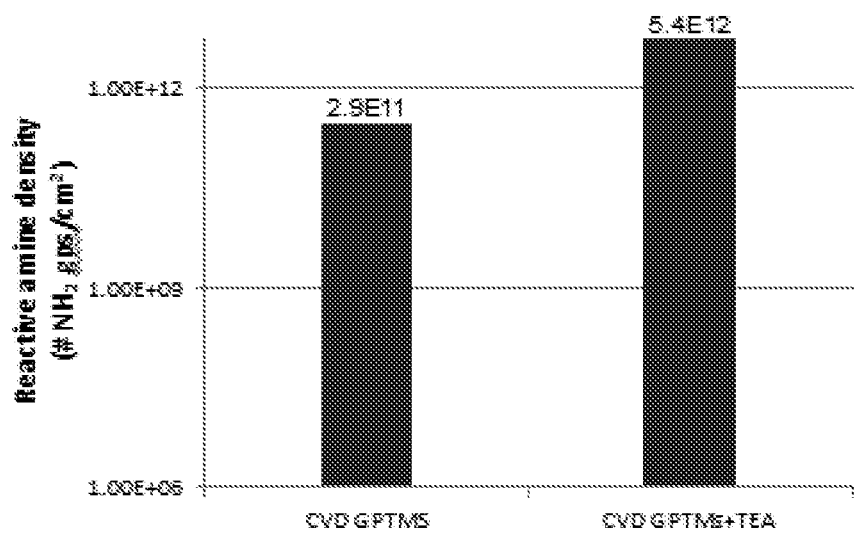
FIG. 4. Depicts the reactive amine density of GPTMS-TEA coating compared to a GPTMS coating.

FIG. 2 illustrates a GPTMS-TAEA molecule.

Example 3—GPTMS-HMDA

Figure 5:
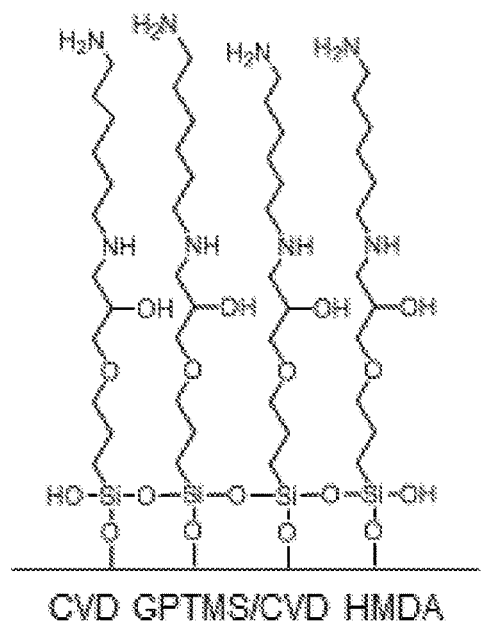
FIG. 5. depicts a GPTMS-HMDA linker prepared by chemical vapor deposition
Figure 6:
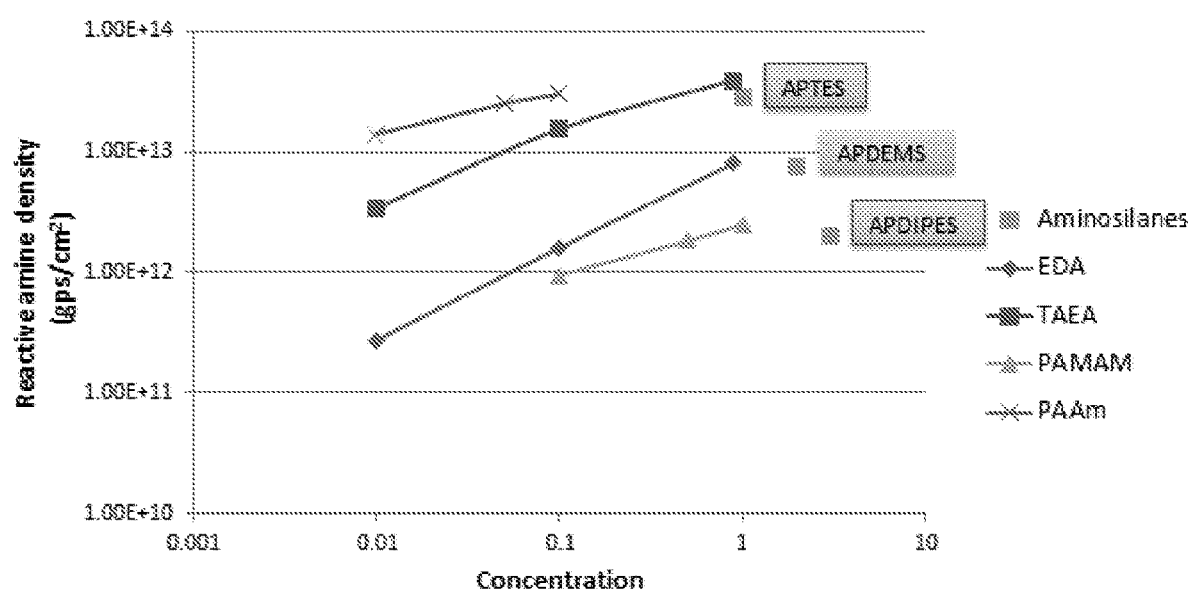
FIG. 6. Depicts reactive amine densities for GPTMS-linked EDA, TAEA, PAMAM, and PAAm amino coatings. Also depicted are reactive amine densities for aminosilane coatings APTES, APDEMS, and APDIPES.
Figure 7:
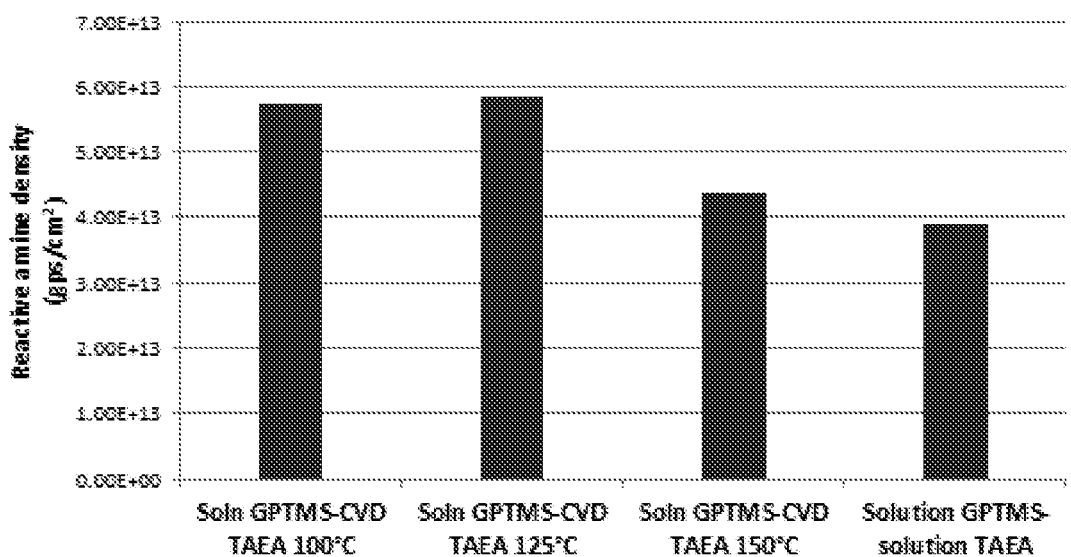
FIG. 7 reactive amine densities for GPTMS-TAEA linkers with chemical vapor deposition performed at 100, 125, and 150 degrees Celcius.
Figure 8:
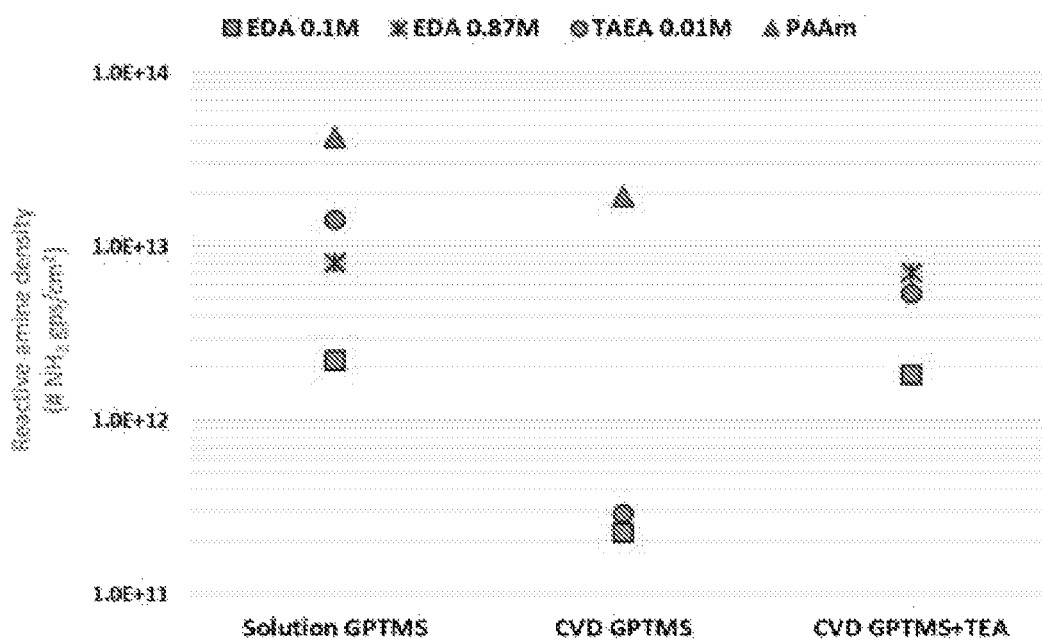
FIG. 8 depicts reactive amine densities from GPTMS-linked EDA, TAEA, and PAAm surface coatings.
Figures 9, 10:
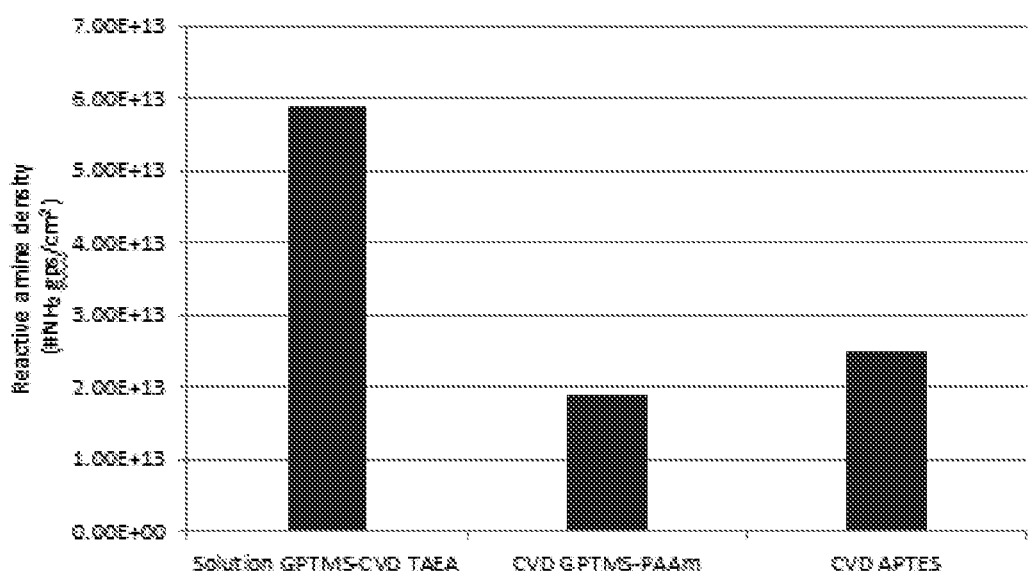
FIG. 9 depicts water contact angle and thickness properties for GPTMS-linked-EDA and Boc-Gly surface coatings at different deposition conditions.
FIG. 10 depicts surface amine densities of GPTMS-TAEA, GPTMS-PAAm, and APTES surface coatings.
Figure 11:
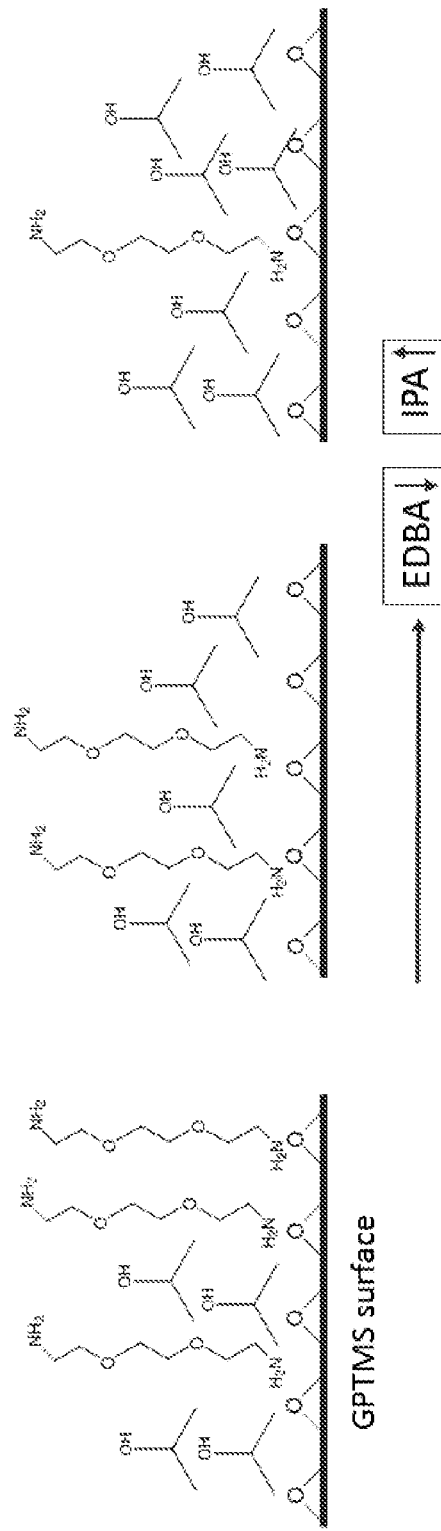
FIG. 11 depicts the use of a diluent to tune the reaction of forming second coating layer.
Figure 13:
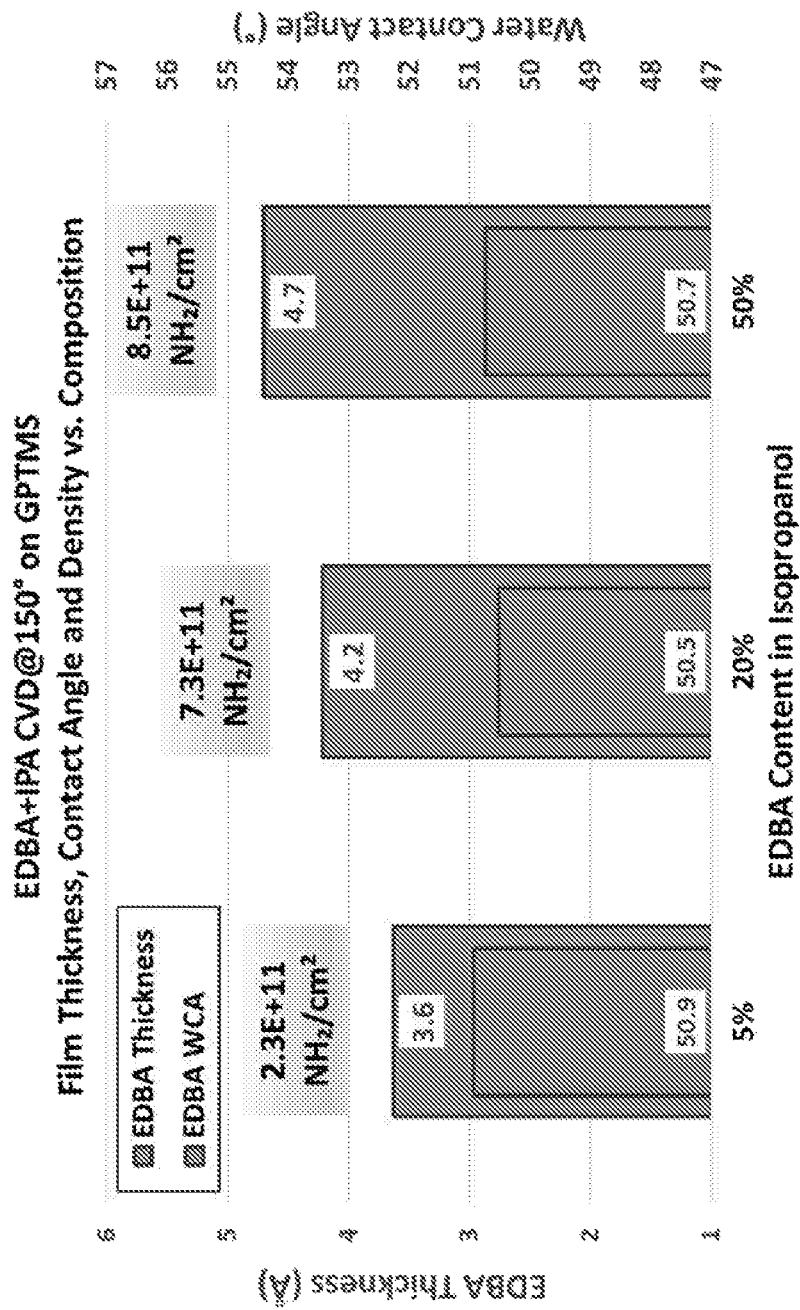
FIG. 13 depicts thickness and water contact angle analysis of amino coatings produced with a diluent in the formation of the second coating layer.
Figure 14:
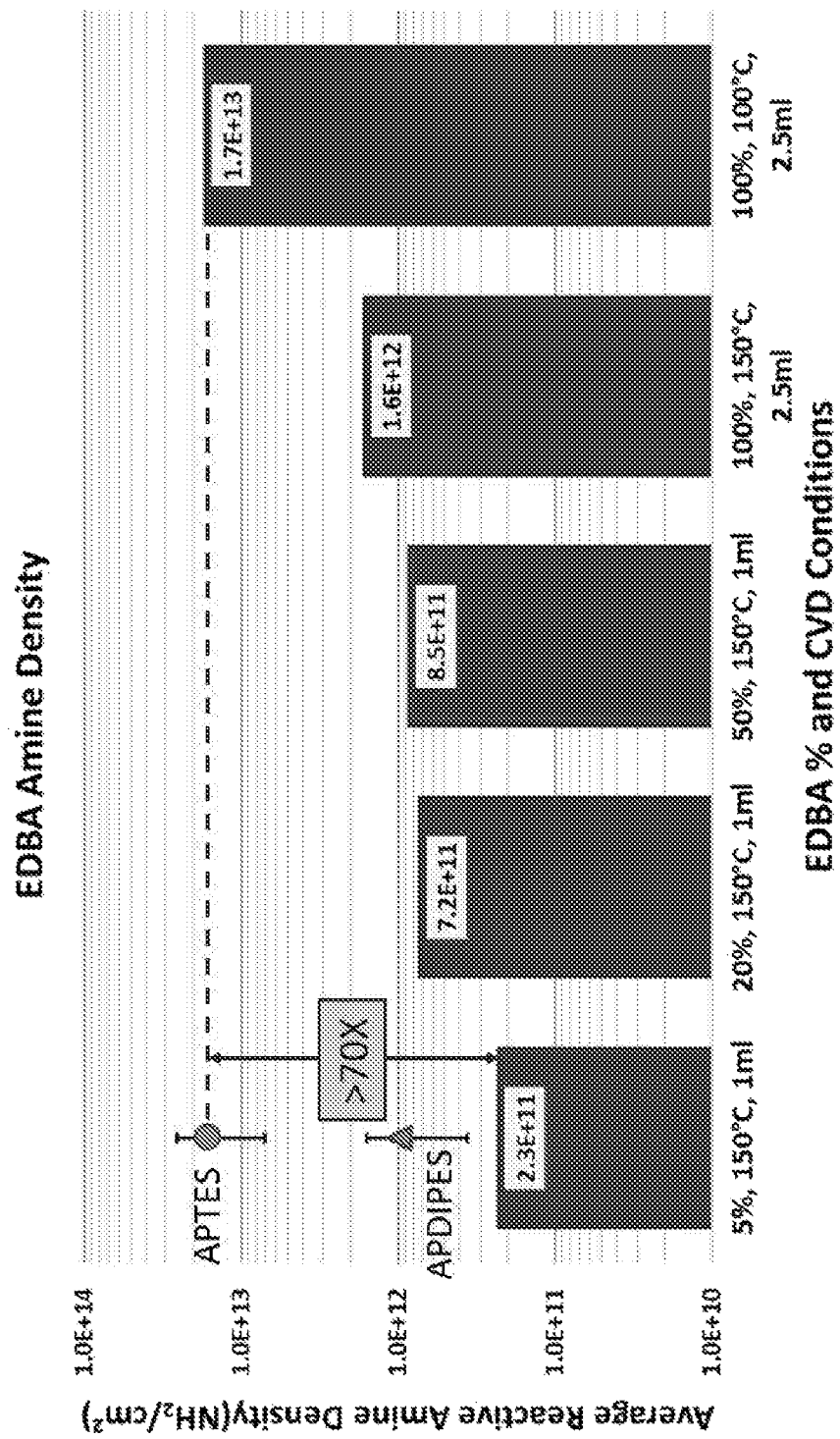
FIG. 14 depicts reactive amine density of amino coatings under various reaction conditions.
Figure 15:
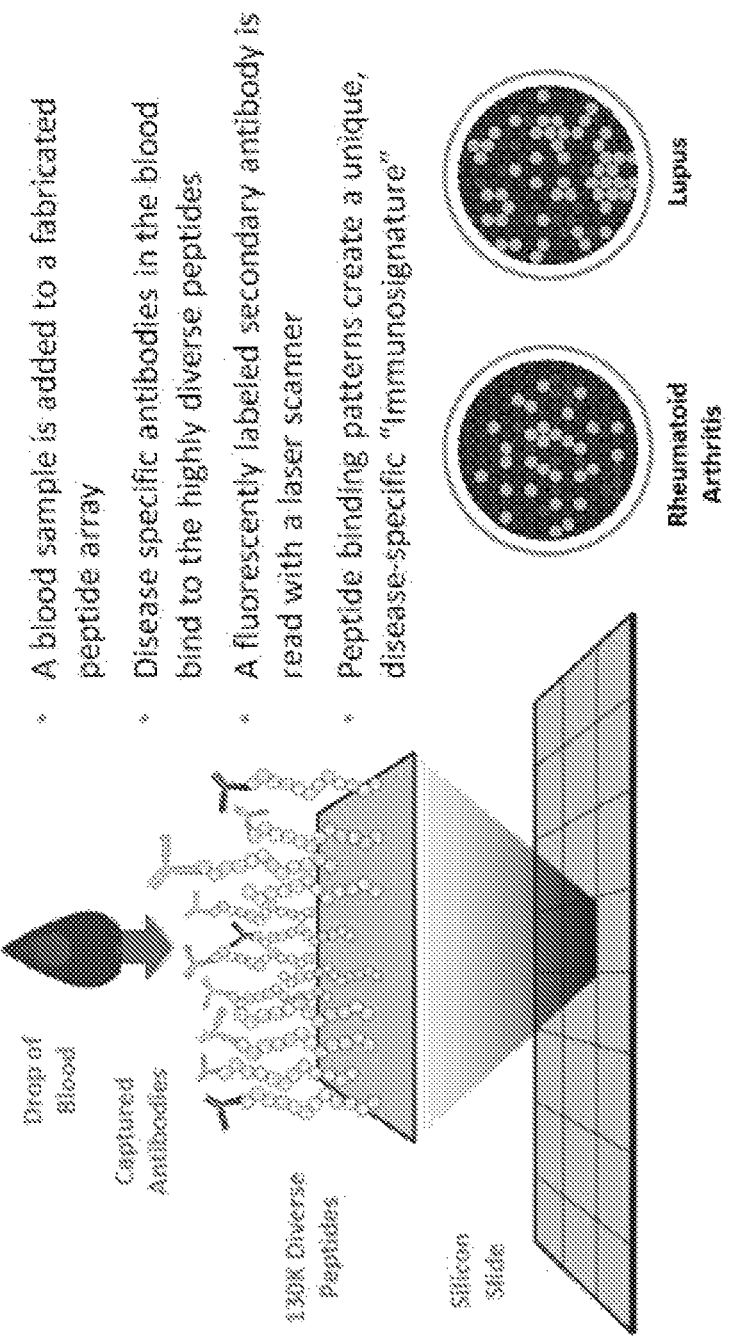
FIG. 15 depicts the use of a molecular array for immunosignaturing.
Figure 16:
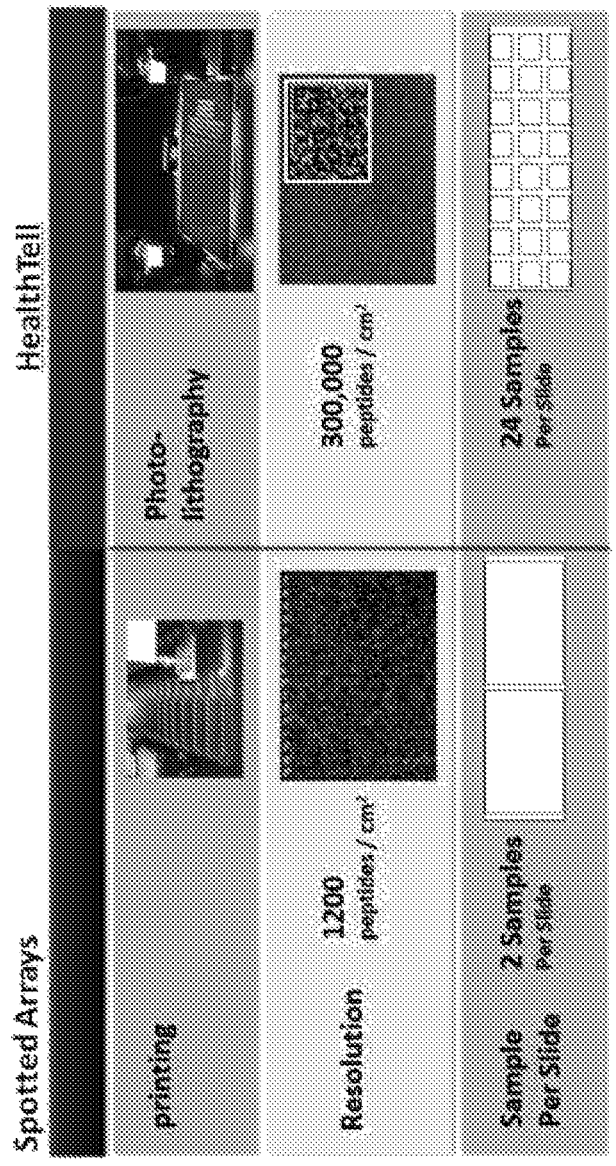
FIG. 16 depicts the arrangement of features on a molecular array.
Figure 18:
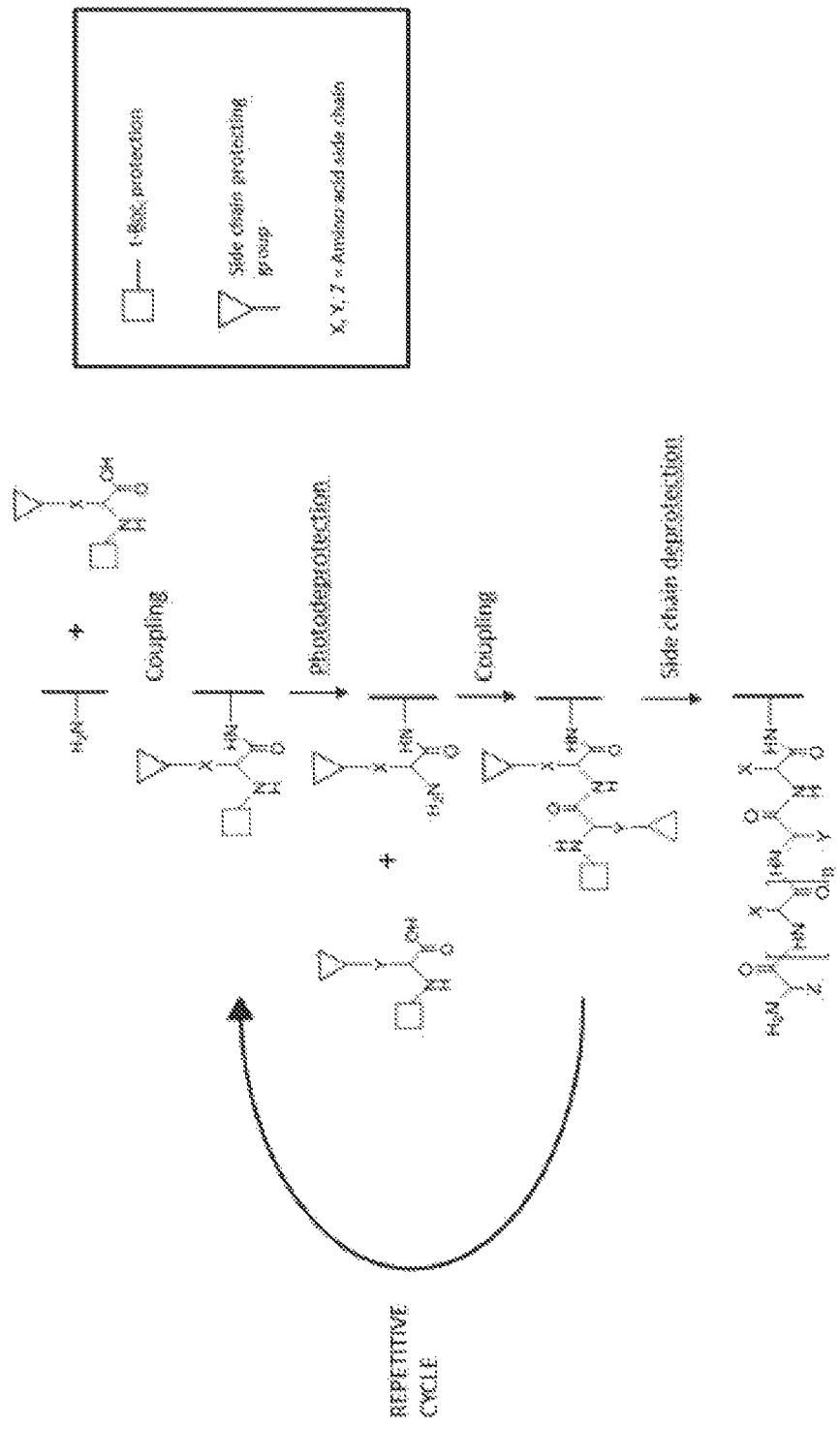
FIG. 18 depicts a scheme for peptide synthesis.
Figure 19:
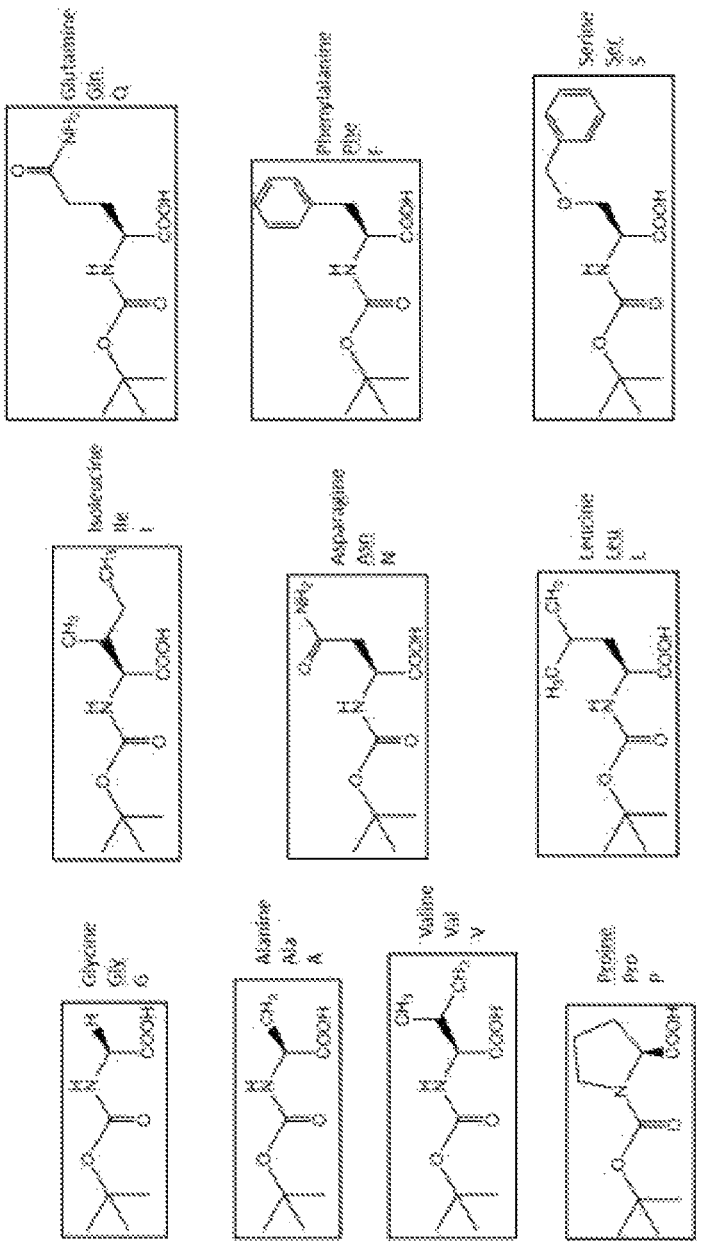
FIG. 19 depicts protected amino acids.
Figure 20:
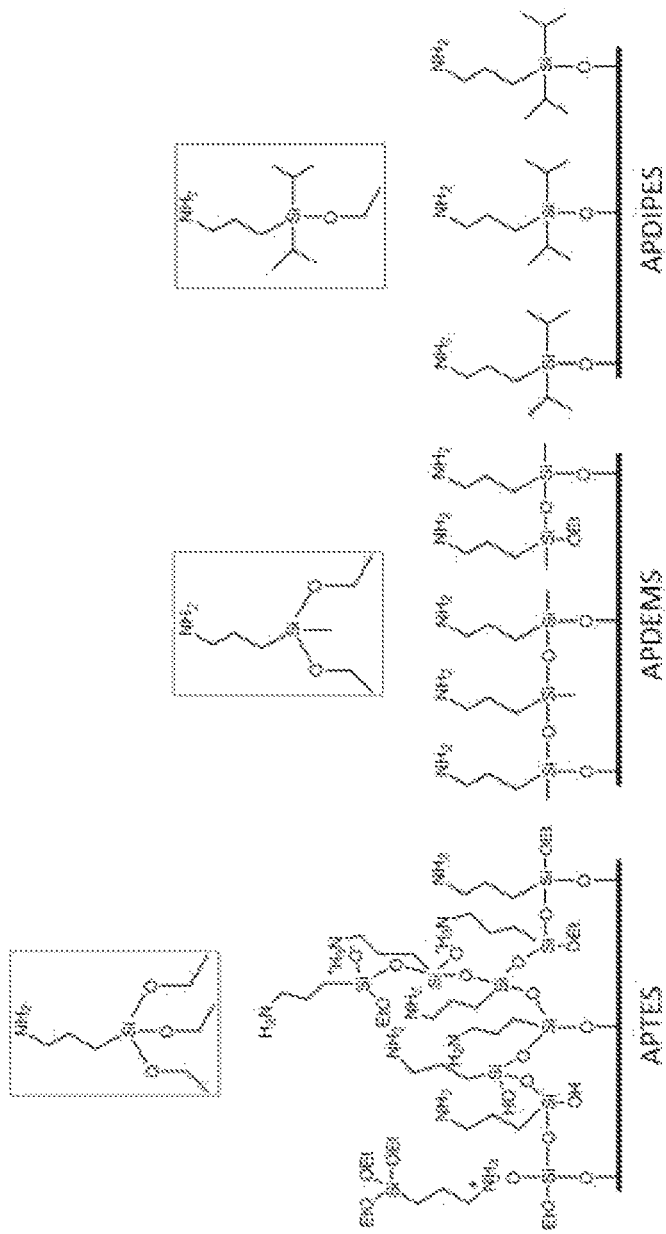
FIG. 20 depicts aminosilane coating structures.
Figure 22:
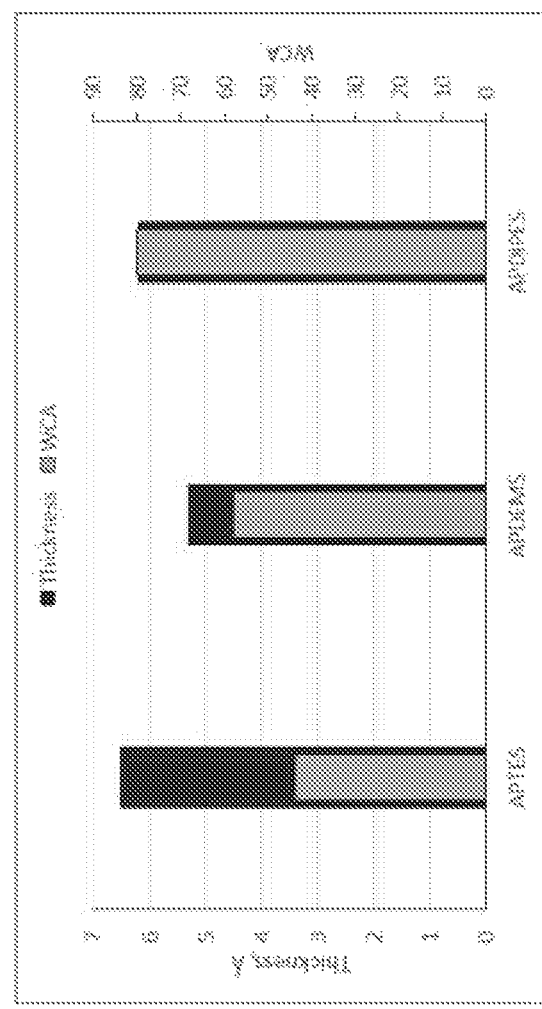
FIG. 22 depicts thickness and water contact angle analysis of amino coatings.
Figure 23:
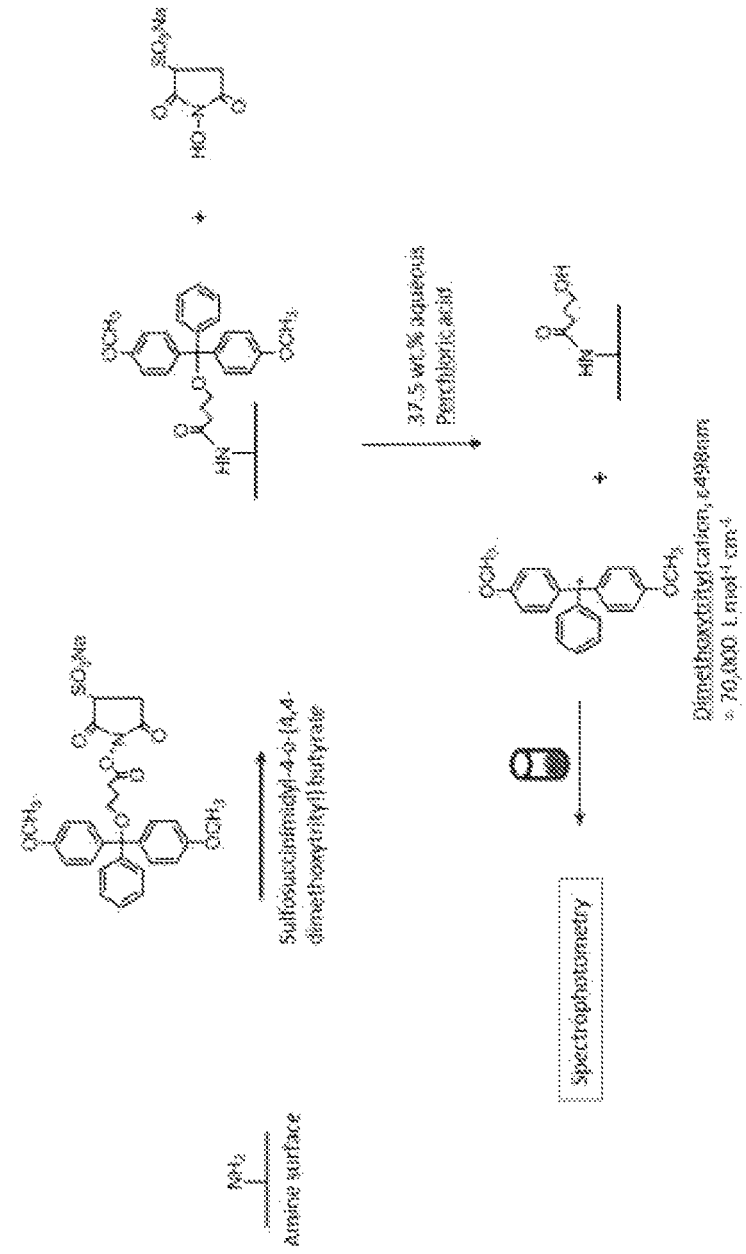
FIG. 23 depicts a scheme for a reactive amine density assay.
Figure 24:
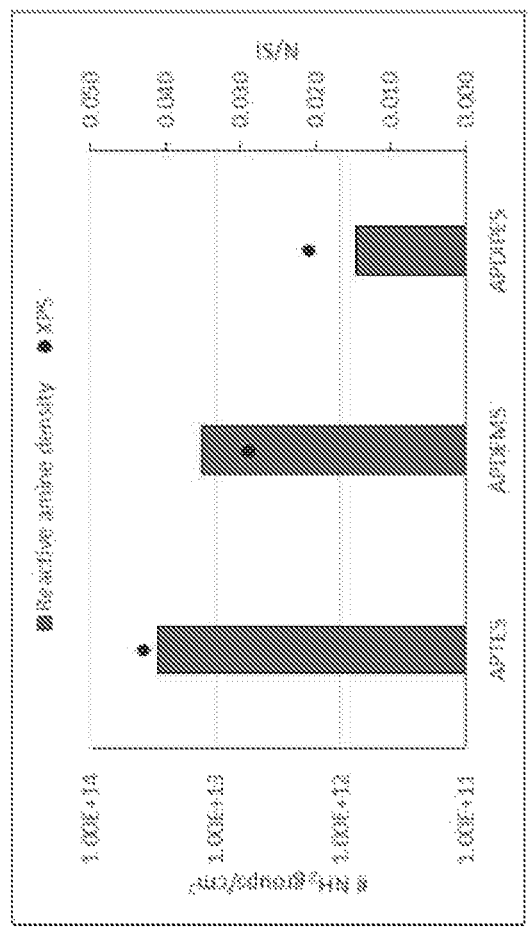
FIG. 24 depicts an amine density analysis of amino coatings.
Figure 25:
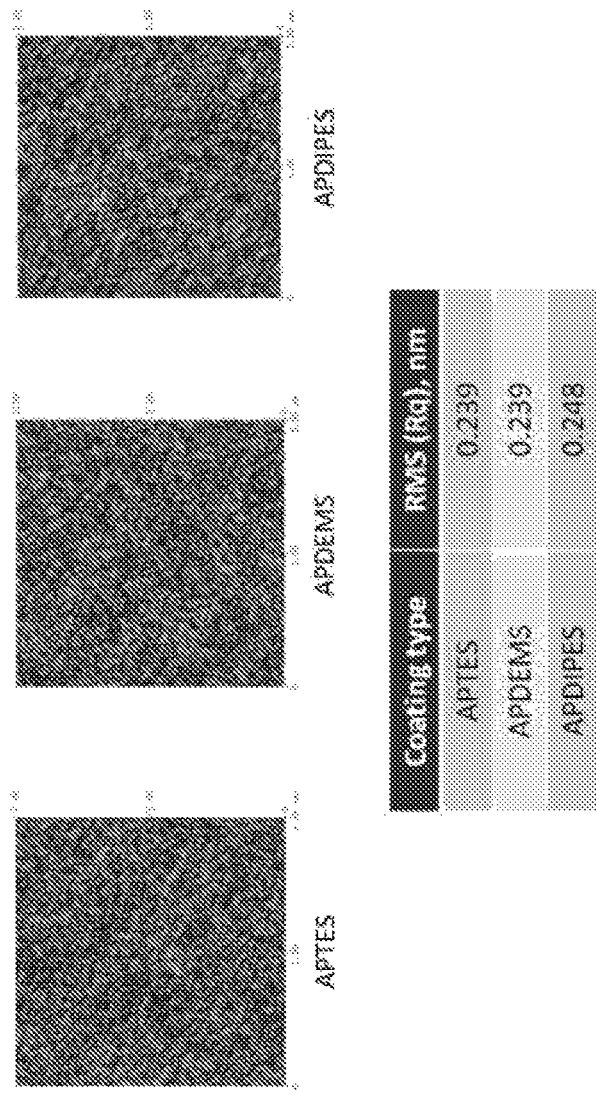
FIG. 25 depicts an AFM analysis of the smoothness of deposition of amino coatings.
Figure 28:
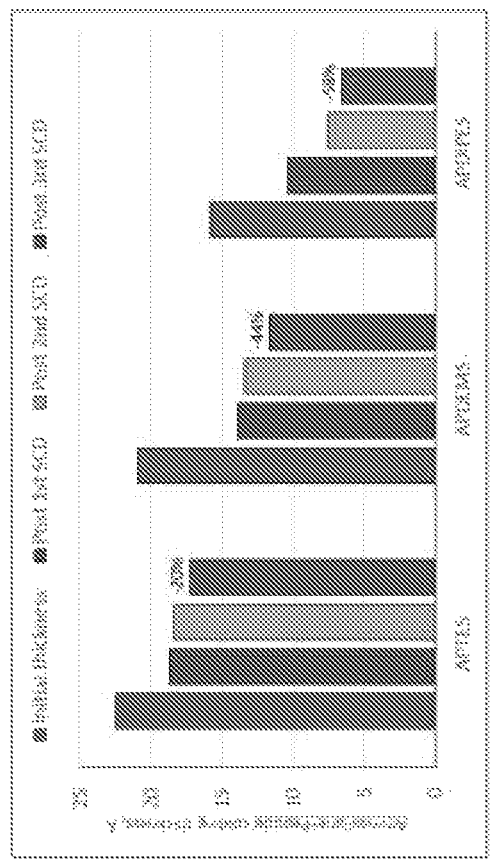
FIG. 28 depicts a thickness analysis of peptide-functionalized amino coatings.
Figure 29:
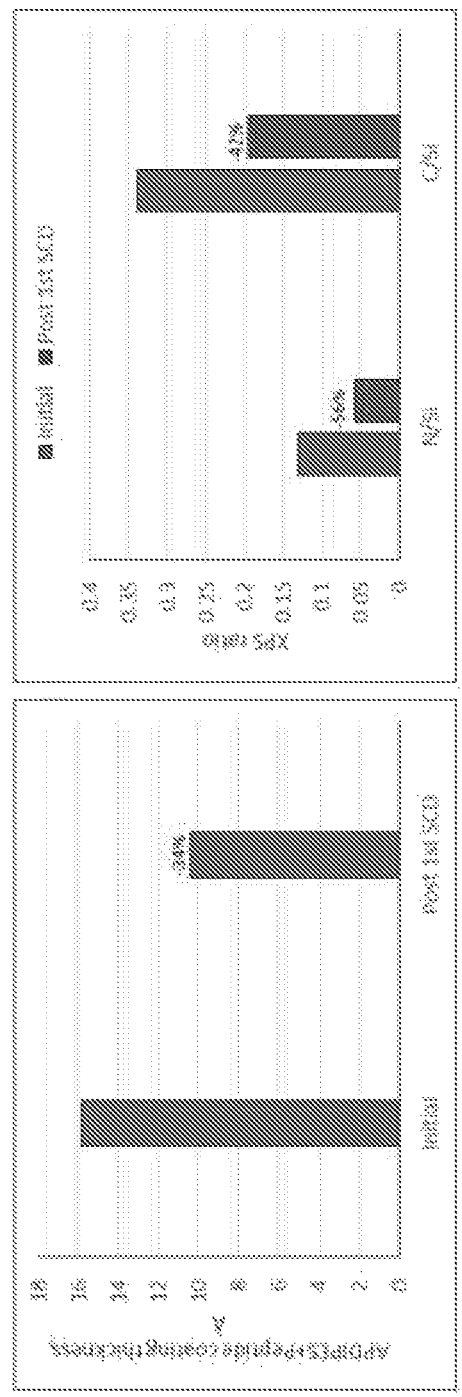
FIG. 29 depicts thickness and XPS analysis of amino coatings.
Figure 30:
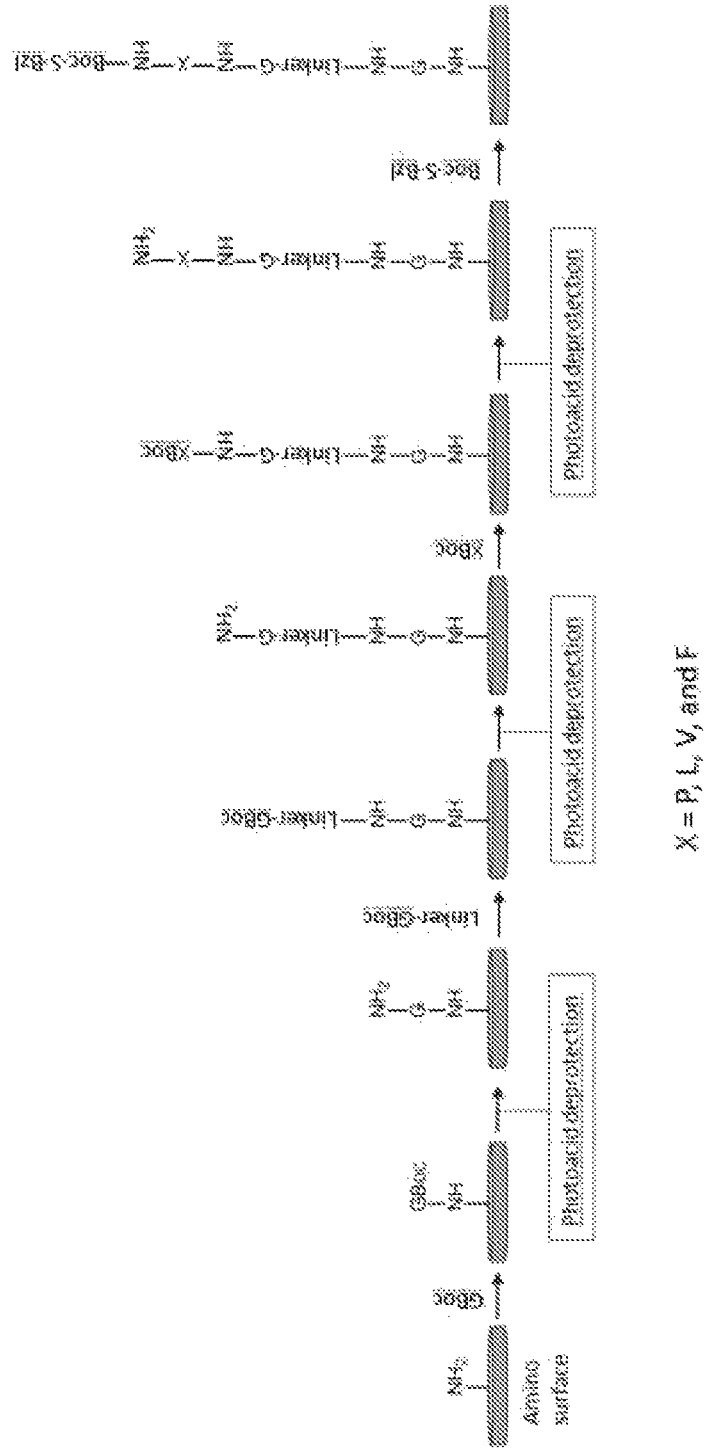
FIG. 30 depicts a scheme for peptide synthesis, amine capping, and MALDI-MS analysis.
Figure 31:
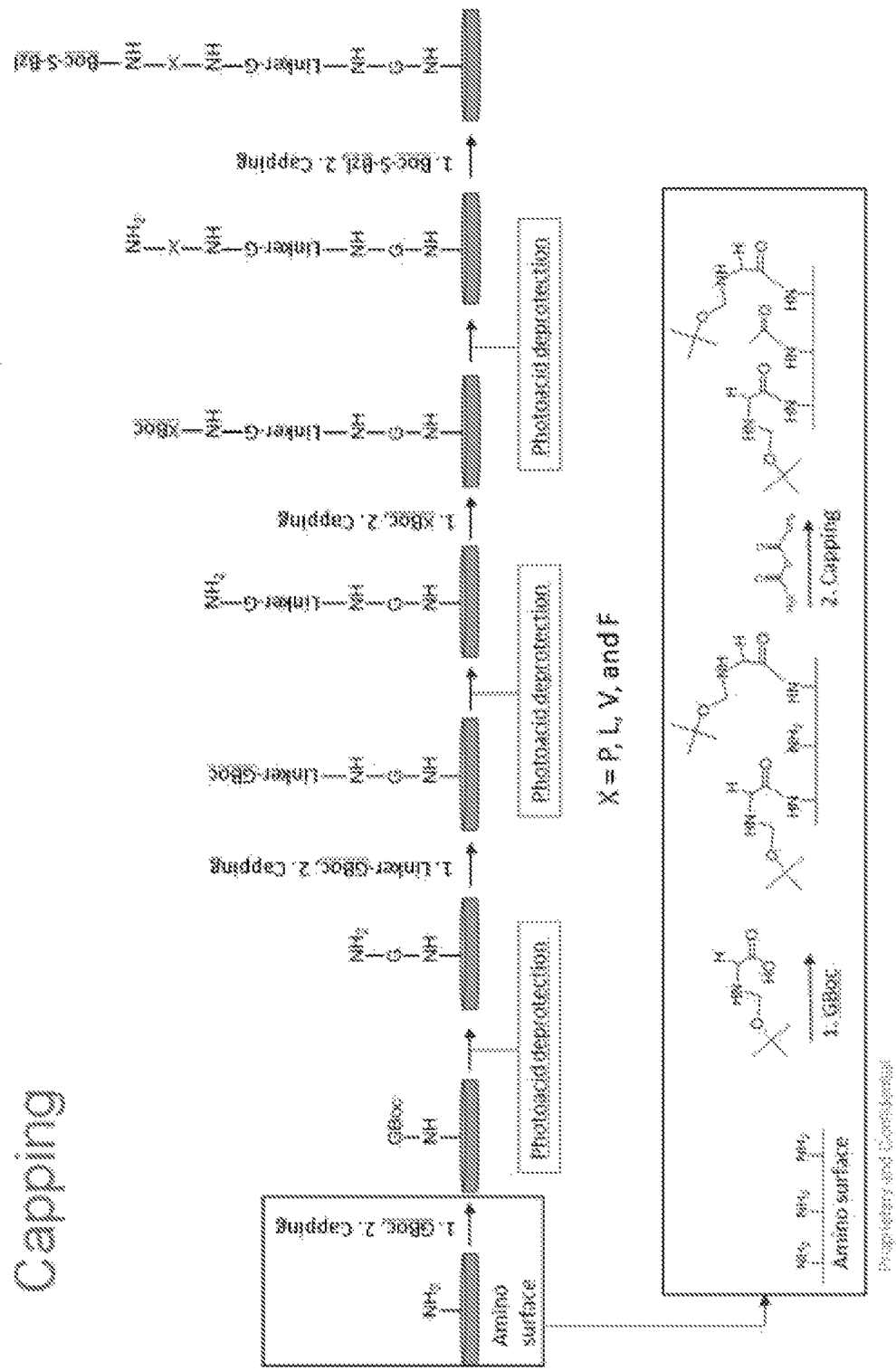
FIG. 31 depicts a scheme for peptide synthesis, amine capping, and MALDI-MS analysis.
Figure 32:
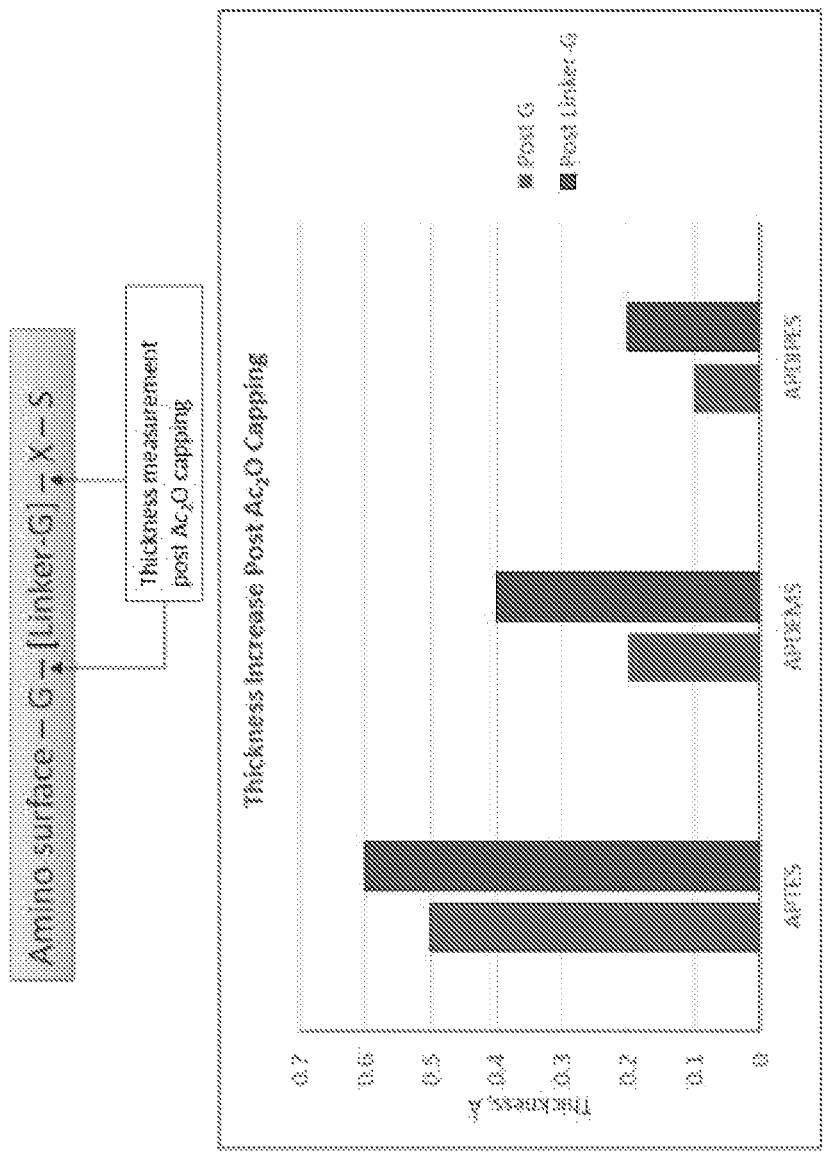
FIG. 32 depicts a thickness analysis of amino coatings.
Figure 33:
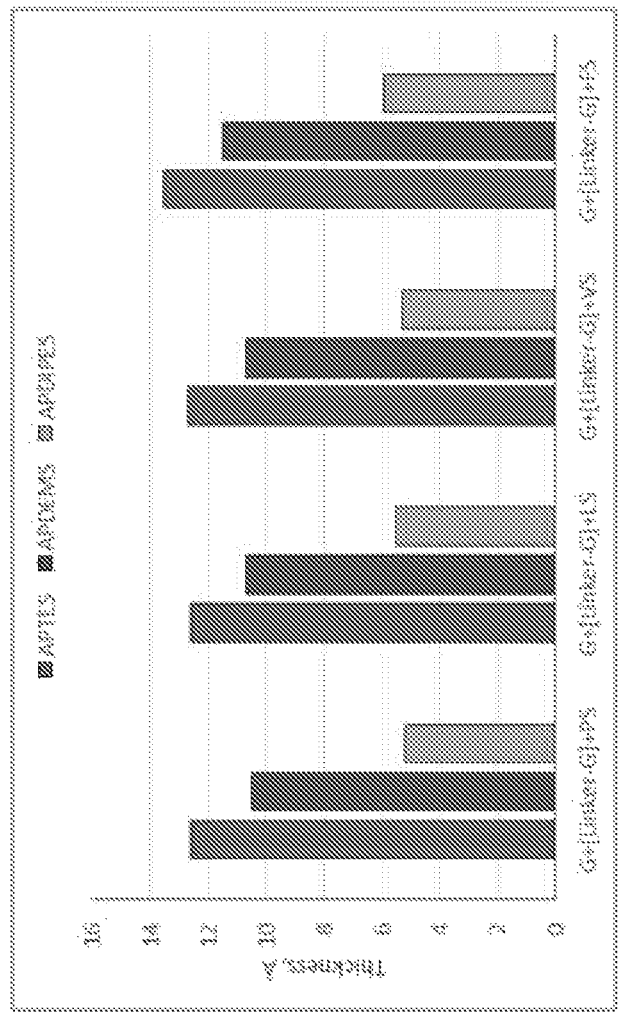
FIG. 33 depicts a thickness analysis of amino coatings.
Figure 34:
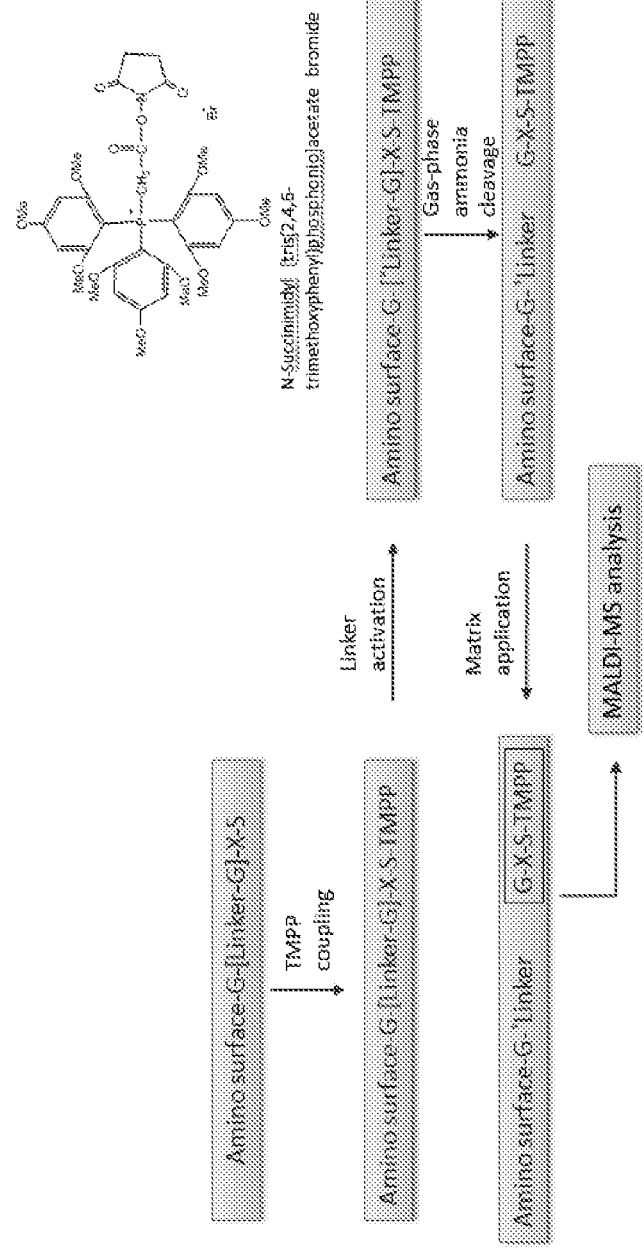
FIG. 34 depicts procedures for surface preparation for MALDI-MS analysis.
Figure 35:
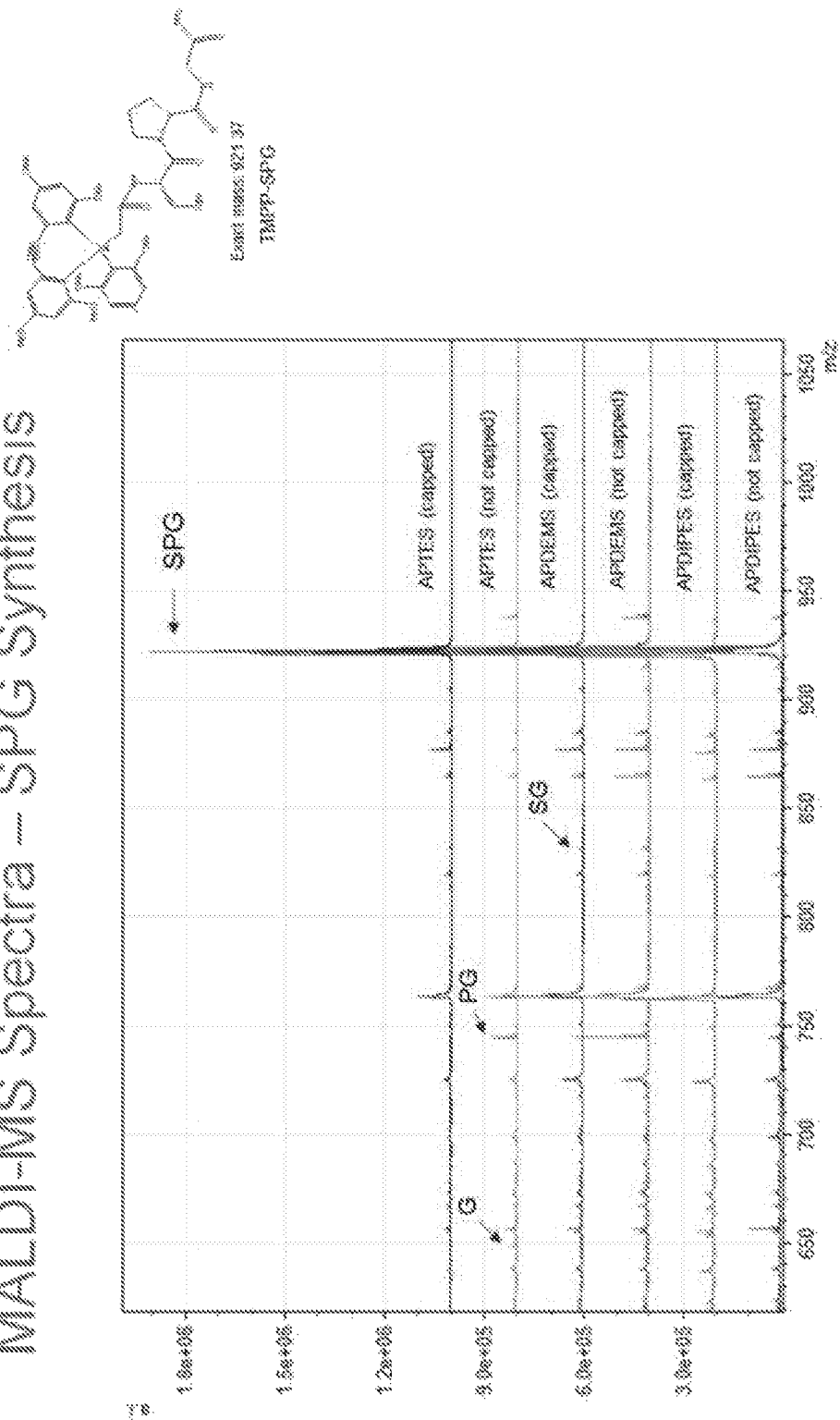
FIG. 35 depicts a MALDI-MS analysis of array coatings.
Figure 36:
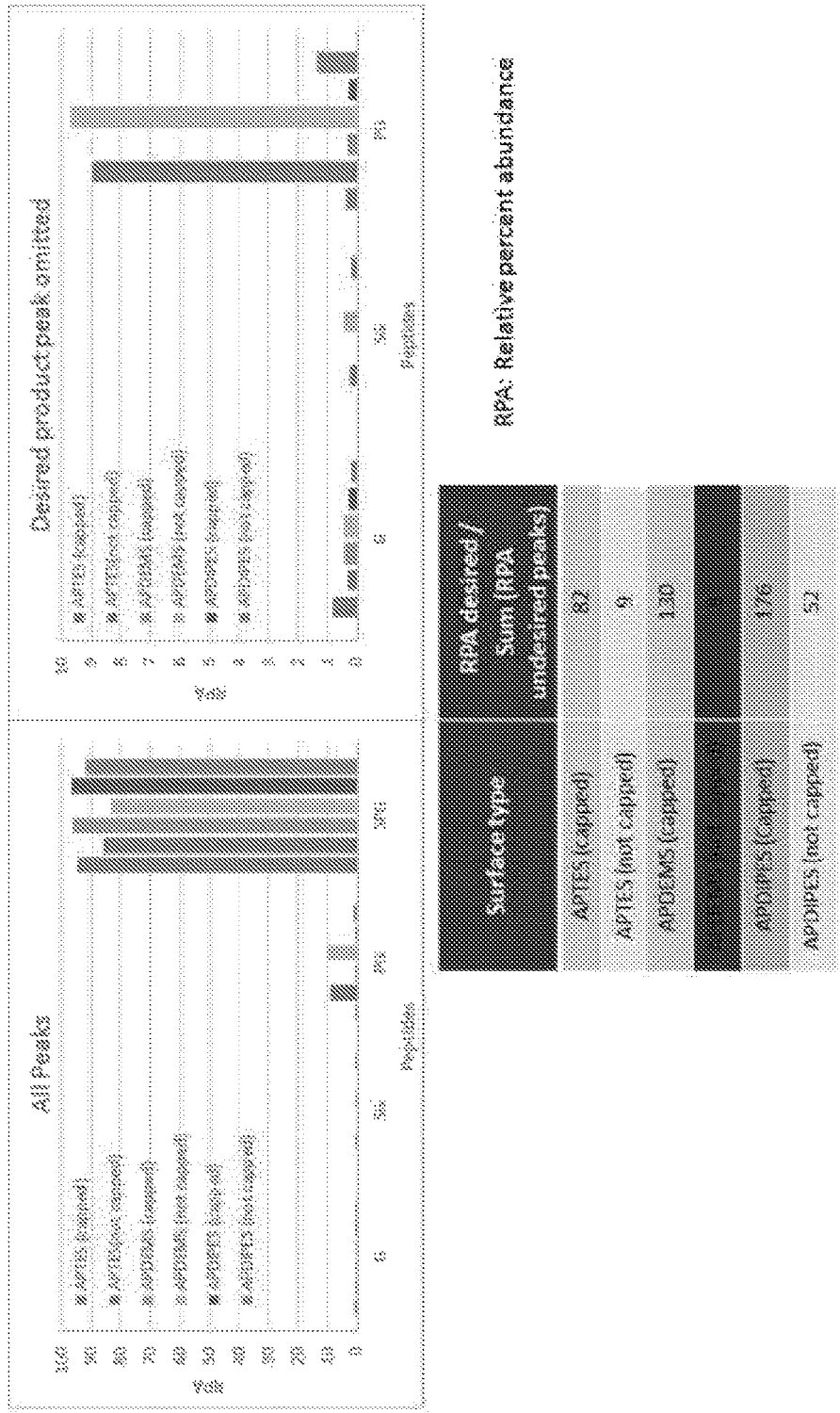
FIG. 36 depicts a purity analysis of peptides synthesized on amino coatings.
Figure 37:
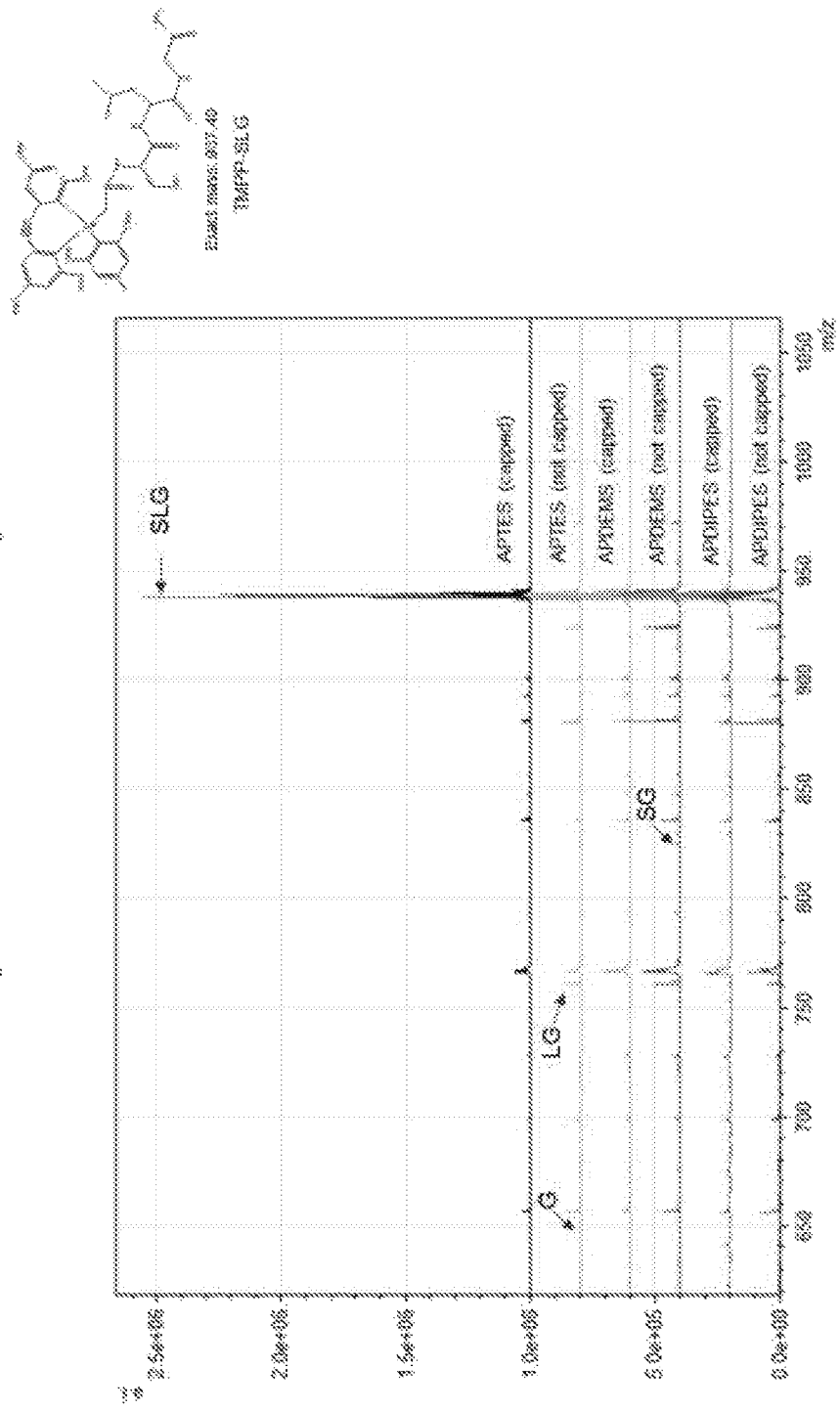
FIG. 37 depicts a MALDI-MS analysis of array coatings.
Figure 38:
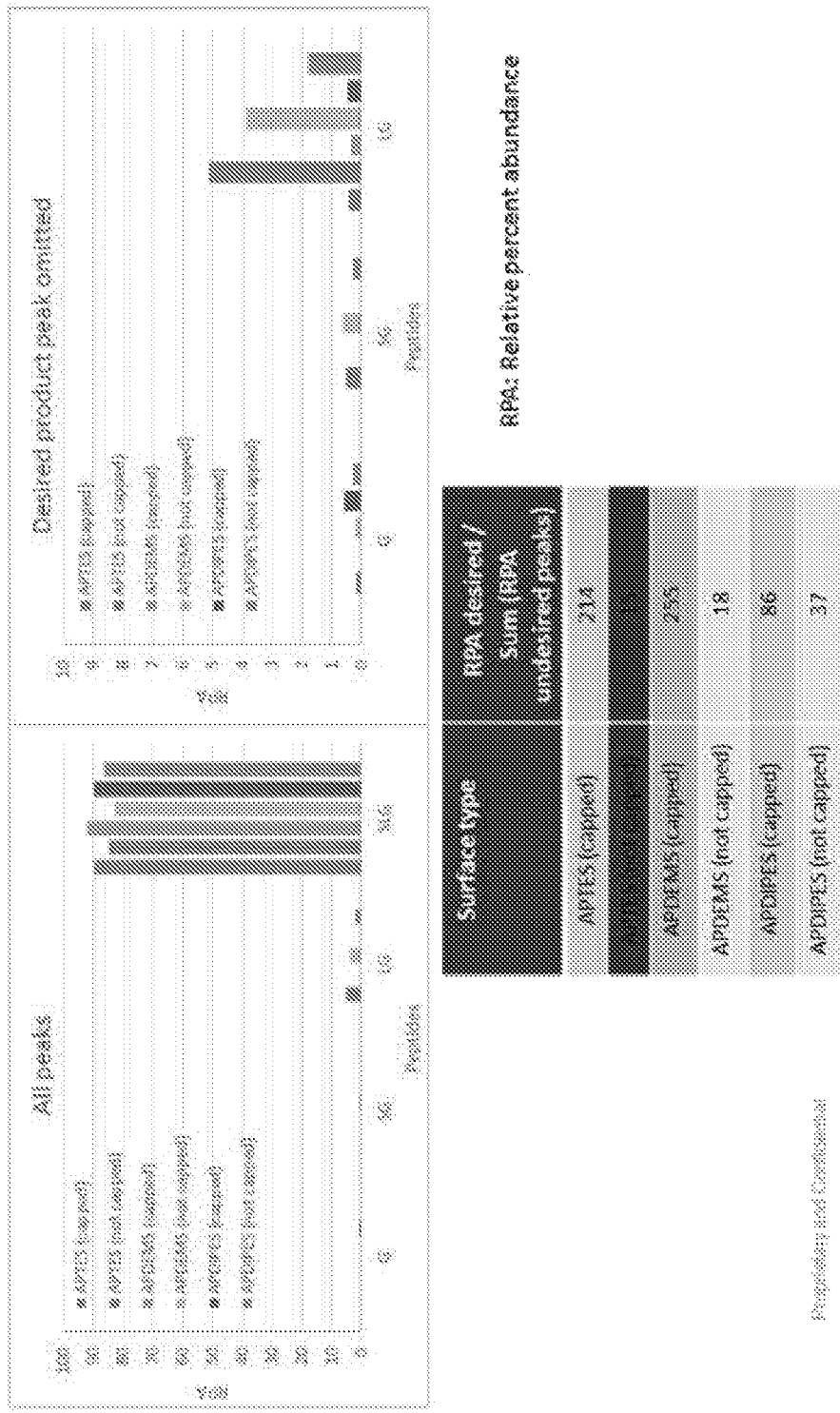
FIG. 38 depicts a purity analysis of peptides synthesized on amino coatings.
Figure 39:
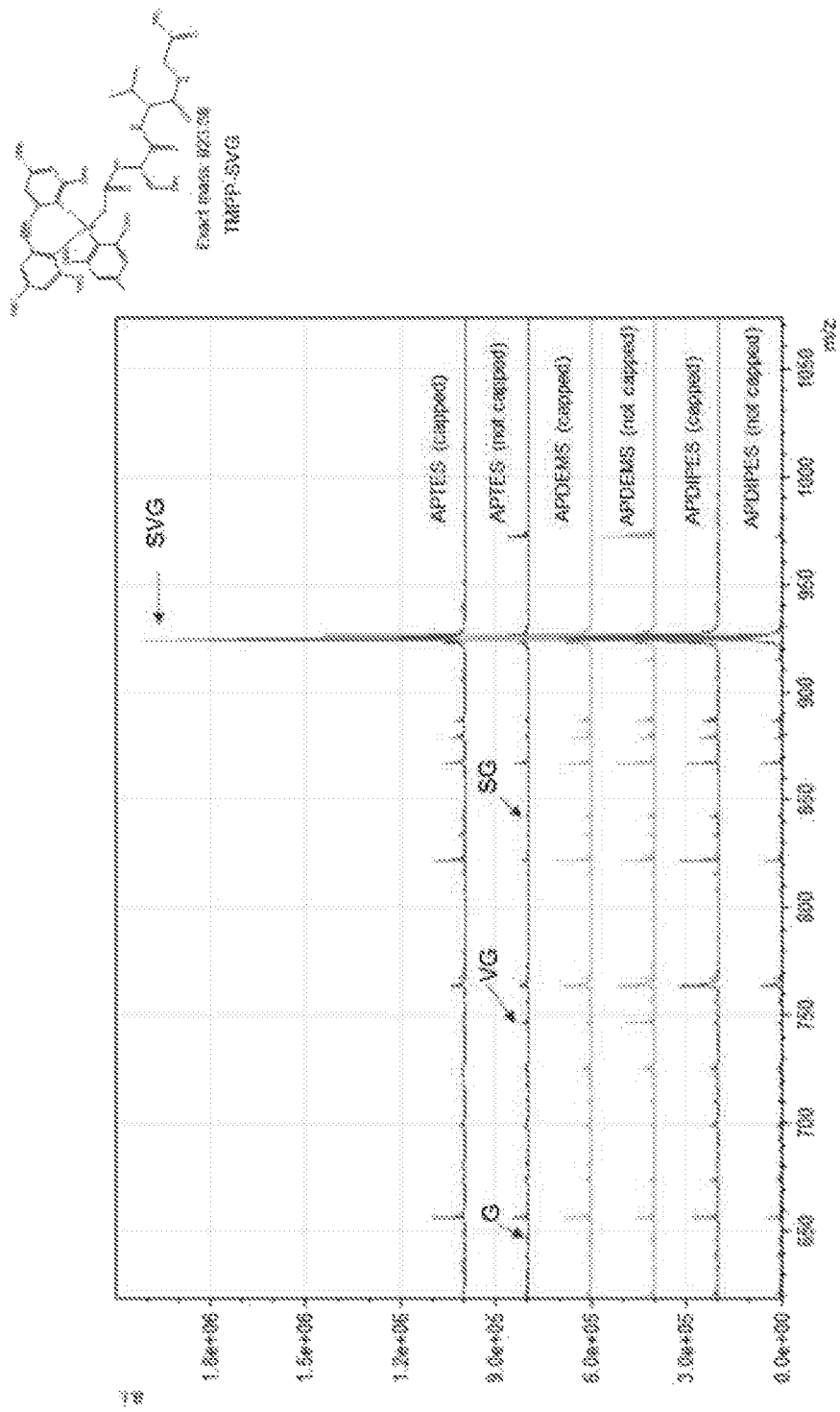
FIG. 39 depicts a MALDI-MS analysis of array coatings.
Figure 40:
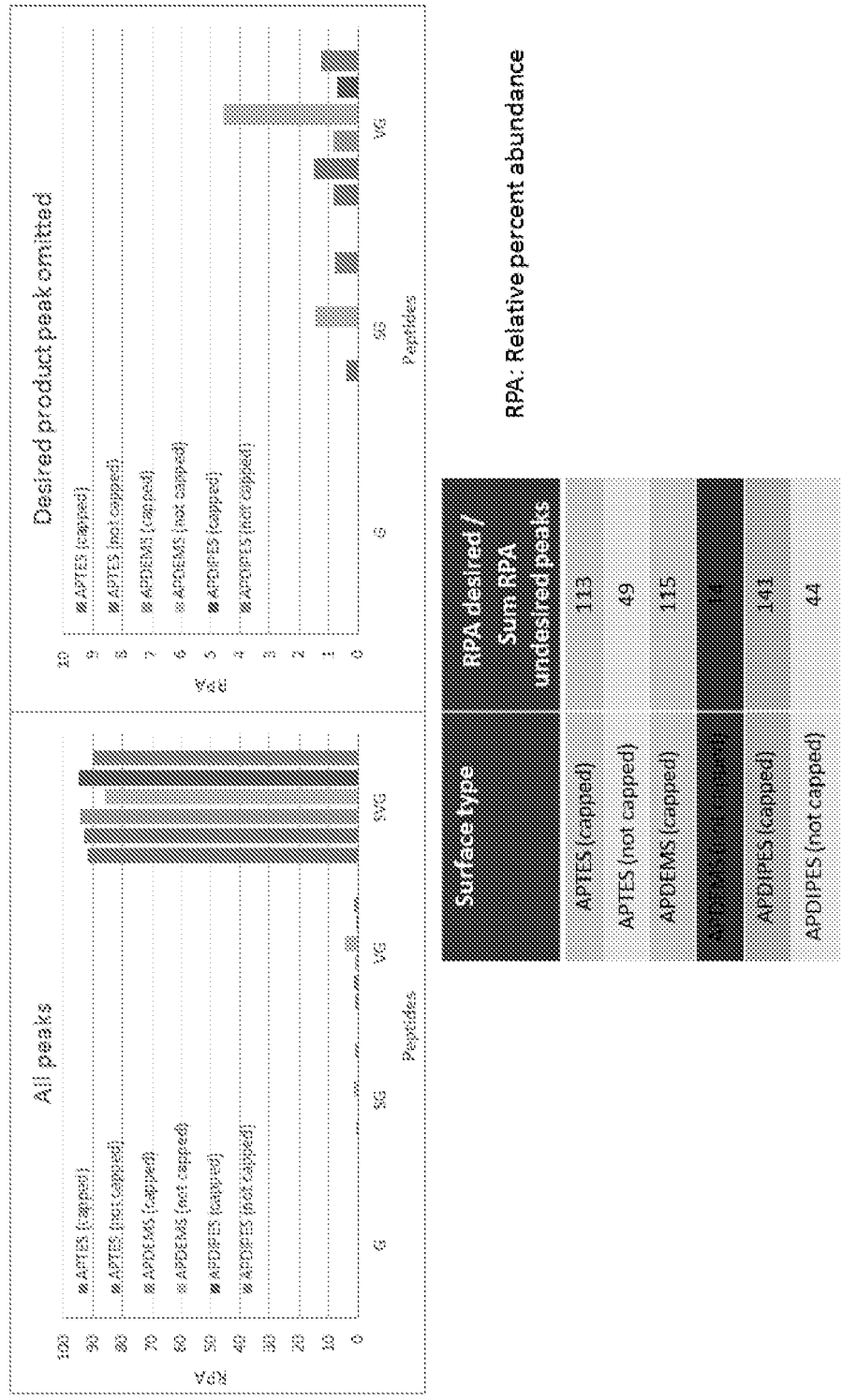
FIG. 40 depicts a purity analysis of peptides synthesized on amino coatings.
Figure 41:
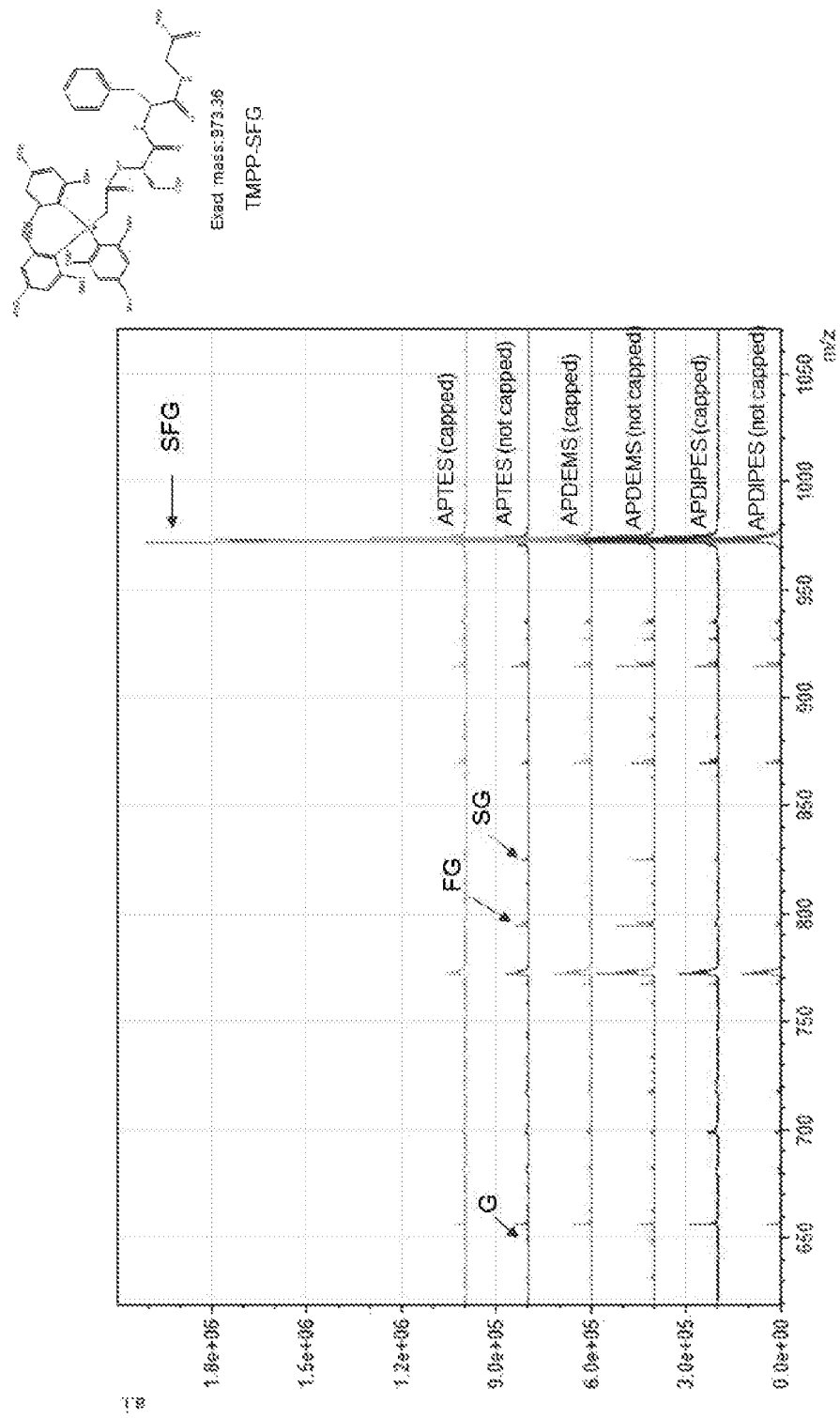
FIG. 41 depicts a MALDI-MS analysis of array coatings.
Figure 42:
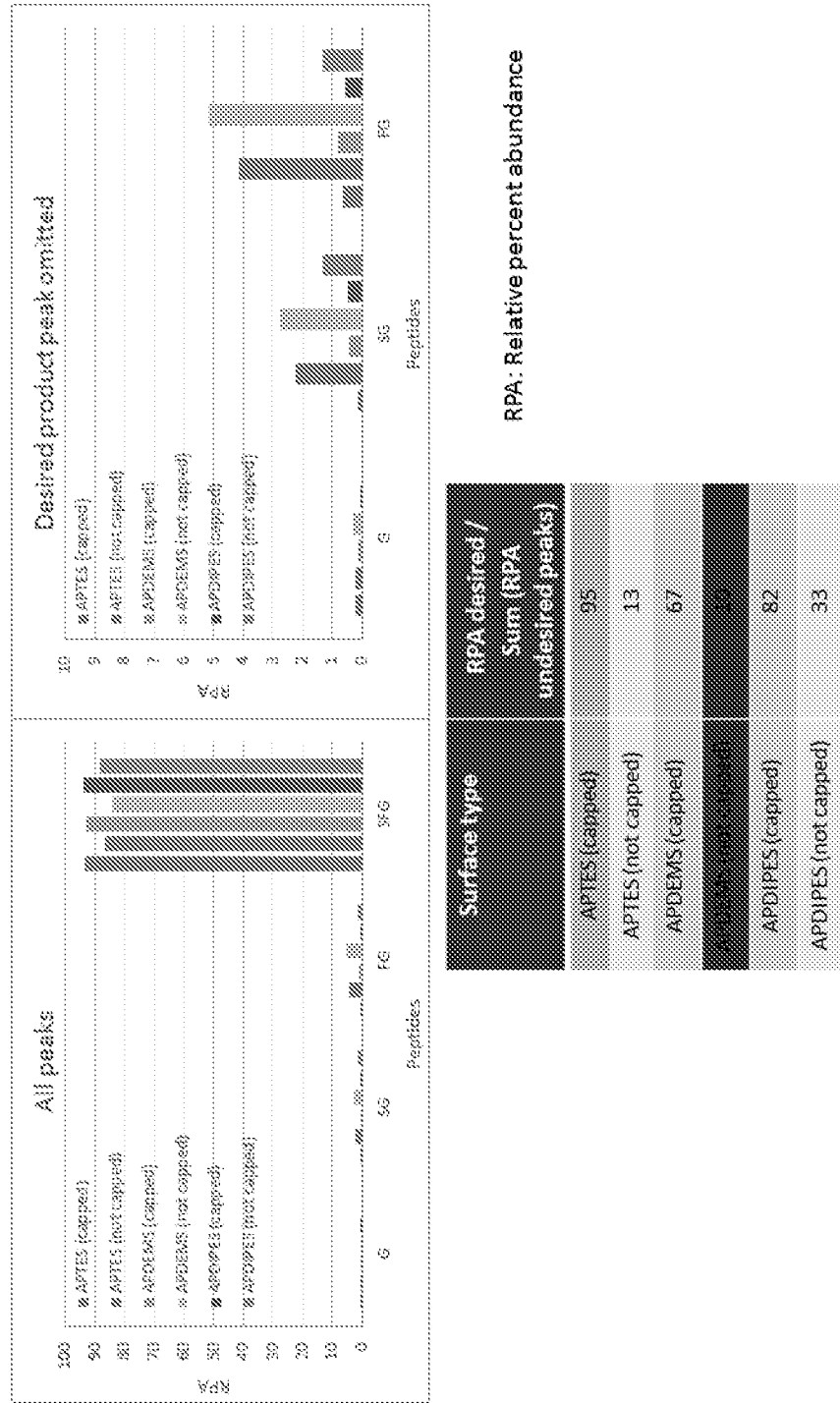
FIG. 42 depicts a purity analysis of peptides synthesized on amino coatings.

FIG. 5 illustrates a GPTMS-HMDA molecule

What is claimed is:

1. An array comprising at least 2 molecules or salts thereof, wherein each of the at least 2 molecules or salts thereof has the structure:

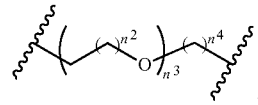

wherein $R^1$ and $R^2$ are the same or different and are independently hydrogen, alkyl, alkenyl, aryl, heteroaryl, alkynyl, arylalkyl, arylalkenyl, haloalkyl, cycloalkyl, sulfonamidyl, acyl, or —$CO_2R^8$, wherein $R^8$ is alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they are bound form a ring; or wherein at least one of $R^1$ or $R^2$ comprise a nucleoside, nucleotide, polynucleotide, peptide, peptoid, saccharide, polysaccharide, aptamer, or antibody or fragment thereof;

$R^3$, oriented from $NR^1R^2$ to NH is alkyl, heteroalkyl, amino-substituted alkyl, amino-substituted heteroalkyl, amidoalkyl, amidoheteroalkyl, amino-substituted amidoheteroalkyl, each optionally substituted with an alkyl, heteroalkyl, amino-substituted alkyl, amino-substituted heteroalkyl, amidoalkyl, amidoheteroalkyl, or amino-substituted amidoheteroalkyl; or wherein $R^3$ is —$(CR^7R^8CR^9R^{10})_n$—, wherein n is 1 to 100, and $R^7$, $R^8$, $R^9$, and $R^{10}$ are the same or different and are hydrogen, halo, alkyl, heteroalkyl, amino-substituted alkyl, amino-substituted heteroalkyl, amidoalkyl, amidoheteroalkyl, amino-substituted amidoheteroalkyl; or wherein $R^3$ is

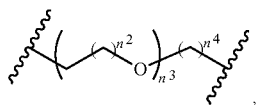

wherein $n^2$ and $n^4$ are the same or different and are independently 1, 2, or 3, and $n^3$ is 1 to 20; or wherein $R^3$ is a polymer or dendrimer comprising alkyl, heteroalkyl, amino-substituted alkyl, amino-substituted heteroalkyl, amidoalkyl, and amino-substituted amidoalkyl, amidoheteroalkyl, or amino-substituted amidoheteroalkyl;

$R^4$, $R^5$, and $R^6$ are the same or different and are independently hydrogen, alkyl, silyl, or siloxy;

(*) is a carbon center, wherein said carbon center is in an R-configuration or S-configuration;

wherein at least one of $R^4$, $R^5$, or $R^6$ further comprises a solid phase, wherein said array comprises a density of reactive amino groups of each molecule or salt thereof on the array of at least about $1 \times 10^{10}$ groups per $cm^2$, and wherein the density of reactive amino groups is measured in the absence of the nucleoside, nucleotide, polynucleotide, peptide, peptoid, saccharide, polysaccharide, aptamer, or antibody or fragment thereof of $R^1$ and $R^2$, and wherein at least some of said molecules or their salts form a coating, wherein said coating has a thickness of from about 1 angstrom to about 25 angstroms.

2. The array claim 1, wherein said carbon center is in an R-configuration.

3. The array of claim 1, wherein said carbon center is in an S-configuration.

4. The array of claim 1, comprising said solid phase.

5. The array of claim 1, wherein said solid phase comprises a silicon atom.

6. The array of claim 1, wherein $R^3$ is alkyl, aminoheteroalkyl, polyamidoaminoalkyl, or polyaminoalkyl.

7. The array of claim 1, wherein said array comprises a density of said amino groups from about $1 \times 10^{10}$ groups per $cm^2$ to about $1 \times 10^{14}$ groups per $cm^2$.

8. The array of claim 1, wherein said molecules or salts are a racemate.

9. The array of claim 1, wherein said molecules or salts have an enantiomeric excess of at least about 10%, 20%, 30%, 40%, 50%, 60%, 70%, 80%, 85%, 90%, 95%, 96%, 97%, 98%, 99%, or 100%.

10. The array of claim 1, wherein said molecules or their salts are cross-linked.

11. An array comprising at least 2 molecules or salts thereof, wherein each of the at least 2 molecules or salts thereof has the structure:

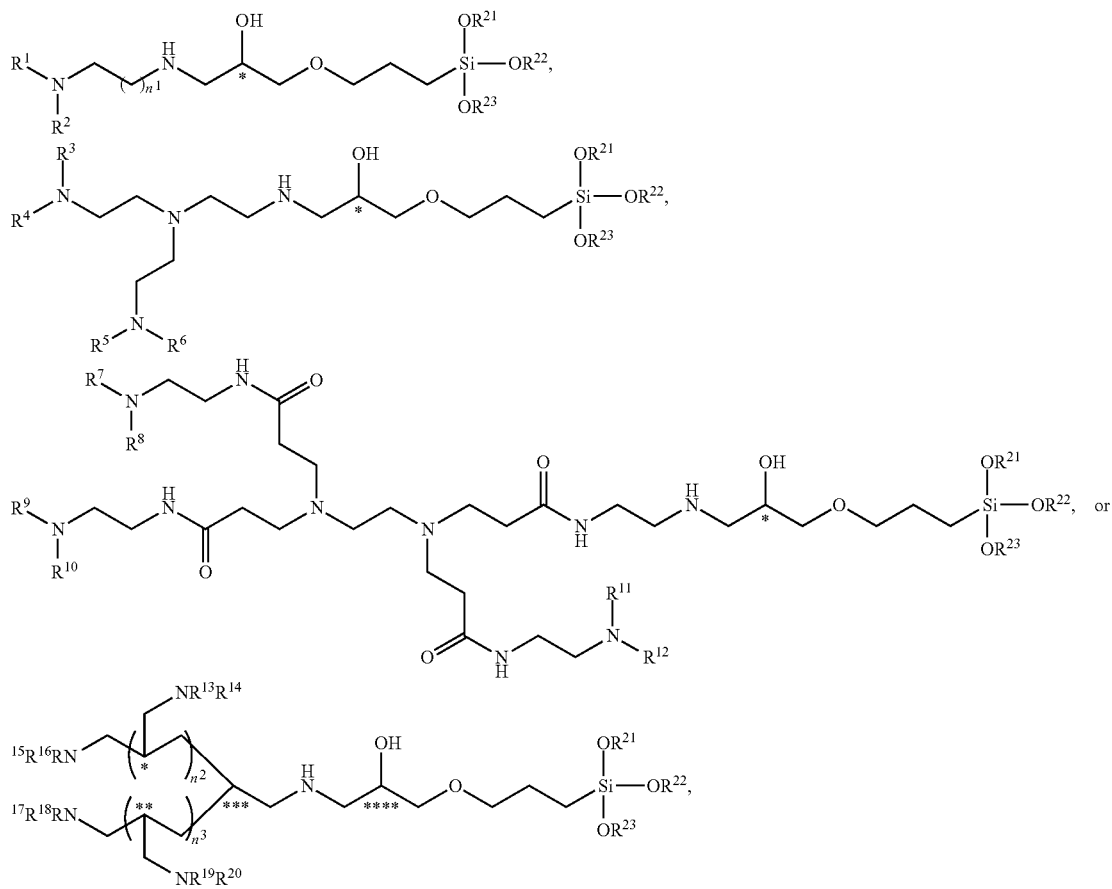

wherein:

$n^1$=1, 2, 3, 4, 5, 6, or 7;

$n^2$ and $n^3$ are the same or different and are independently about 1 to about 1000;

$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}$, and $R^{20}$ are the same or different and are hydrogen, alkyl, alkenyl, aryl, heteroaryl, alkynyl, arylalkyl, arylalkenyl, haloalkyl, cycloalkyl, sulfonamidyl, acyl, or —$CO_2R^{24}$, wherein $R^{24}$ is alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they are bound, $R^3$ and $R^4$ and the N to which they are bound, $R^5$ and $R^6$ and the N to which they are bound, $R^7$ and $R^8$ and the N to which they are bound, $R^9$ and $R^{10}$ and the N to which they are bound, $R^{11}$ and $R^{12}$ and the N to which they are bound, $R^{13}$ and $R^{14}$ and the N to which they are bound, $R^{15}$ and $R^{16}$ and the N to which they are bound, $R^{17}$ and $R^{18}$ and the N to which they are bound, and $R^{19}$ and $R^{20}$ and the N to which they are bound independently optionally form a ring;

$R^3$, $R^4$, and $R^5$ are the same or different and are independently hydrogen, alkyl, silyl, or siloxy;

(*), (), and (*) are carbon centers, wherein said carbon centers are independently in an R-configuration or S-configuration, or can be achiral centers;

(****) is a second carbon center, wherein said second carbon center is in an R-configuration or S-configuration;

wherein at least one of $R^{21}$, $R^{22}$, or $R^{23}$ further comprises a solid phase; and wherein said array comprises a density of amino groups of each molecule or salt thereof on the array of at least about $1 \times 10^{10}$ groups per $cm^2$.

12. The array of claim 11, wherein said carbon center is in an R-configuration.

13. The array of claim 11, wherein said carbon center is in an S-configuration.

14. The array of claim 11, comprising a solid phase.

15. The array of claim 11, wherein said solid phase comprises a silicon atom.

16. The array of claim 11, wherein said array comprises a density of said amino groups from about $1 \times 10^{10}$ groups per $cm^2$ to about $1 \times 10^{14}$ groups per $cm^2$.

17. The array of claim 11, wherein said molecules or salts are a racemate.

18. The array of claim 11, wherein at least some of said molecules or their salts form a coating, wherein said coating has a thickness of from about 1 angstrom to about 25 angstroms.

19. The array of claim 11, wherein said molecules or their salts are cross-linked.

* * * * *